United States Patent
Stad

(10) Patent No.: US 10,888,359 B2
(45) Date of Patent: Jan. 12, 2021

(54) METHODS AND DEVICES FOR POLYAXIAL SCREW ALIGNMENT

(71) Applicant: DePuy Synthes Products, Inc., Raynham, MA (US)

(72) Inventor: Shawn D. Stad, Fall River, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 29 days.

(21) Appl. No.: 15/984,750

(22) Filed: May 21, 2018

(65) Prior Publication Data
US 2019/0090908 A1    Mar. 28, 2019

Related U.S. Application Data

(63) Continuation of application No. 14/961,065, filed on Dec. 7, 2015, now Pat. No. 9,999,448, which is a
(Continued)

(51) Int. Cl.
*A61B 17/70*  (2006.01)
*A61B 34/20*  (2016.01)
(Continued)

(52) U.S. Cl.
CPC ...... *A61B 17/7077* (2013.01); *A61B 17/7002* (2013.01); *A61B 17/708* (2013.01);
(Continued)

(58) Field of Classification Search
CPC ............ A61B 17/7077; A61B 17/7079; A61B 17/708
See application file for complete search history.

(56) References Cited

U.S. PATENT DOCUMENTS 2,800,829 A    7/1957  West
5,251,127 A   10/1993  Raab
(Continued)

FOREIGN PATENT DOCUMENTS

EP    2 901 957 A1    8/2015
WO    1999015097 A2   4/1999
(Continued)

OTHER PUBLICATIONS

[No Author Listed] Surgical Technique Guide and Ordering Information. DePuy Spine Inc. Sep. 2011. 24 pages.
(Continued)

*Primary Examiner* — Julianna N Harvey
(74) *Attorney, Agent, or Firm* — Nutter McClennen & Fish LLP

(57) ABSTRACT

Devices and methods for aligning the components of polyaxial screws are described herein. In one embodiment, an alignment instrument includes an elongate frame having a longitudinal axis and a plurality of connection caps slidably disposed along the elongate frame. Each connection cap can removably couple to a polyaxial screw extension tube and selectively lock relative to the elongate frame such that a distance between the plurality of connection caps and an angular orientation of each connection cap relative to the elongate frame is maintained. The instrument can also include a transverse angle indicator to indicate an angular orientation of the elongate frame in a plane transverse to the longitudinal axis of the elongate frame. The device can, for example, capture the orientation of a plurality of polyaxial screws during spinal surgery such that the screws can be returned to the same orientation after manipulation to correct a spinal deformity, etc.

12 Claims, 22 Drawing Sheets

Related U.S. Application Data continuation of application No. 13/830,548, filed on Mar. 14, 2013, now Pat. No. 9,241,742.

(51) Int. Cl.
 A61B 17/00 (2006.01)
 A61B 90/00 (2016.01)

(52) U.S. Cl.
 CPC ...... *A61B 17/7035* (2013.01); *A61B 17/7074* (2013.01); *A61B 17/7076* (2013.01); *A61B 90/06* (2016.02); *A61B 2017/00221* (2013.01); *A61B 2034/2072* (2016.02); *A61B 2090/067* (2016.02); *A61B 2562/0219* (2013.01)

(56) References Cited

U.S. PATENT DOCUMENTS

| | | | |
|---|---|---|---|
| 5,291,901 A | 3/1994 | Graf | |
| 5,305,203 A | 4/1994 | Raab | |
| 5,329,933 A | 7/1994 | Graf | |
| 5,672,176 A | 9/1997 | Biedermann et al. | |
| 5,748,767 A | 5/1998 | Raab | |
| 5,957,645 A | 9/1999 | Stacy | |
| 6,015,409 A | 1/2000 | Jackson | |
| 6,302,890 B1 | 10/2001 | Leone, Jr. | |
| 6,340,363 B1* | 1/2002 | Bolger | A61B 17/0206 606/102 |
| 6,554,834 B1 | 4/2003 | Crozet et al. | |
| 6,565,519 B2 | 5/2003 | Benesh | |
| 6,711,432 B1 | 3/2004 | Krause et al. | |
| 6,715,213 B2 | 4/2004 | Richter | |
| 6,736,820 B2 | 5/2004 | Biedermann et al. | |
| 6,974,460 B2 | 12/2005 | Carbone et al. | |
| 7,001,346 B2 | 2/2006 | White | |
| 7,139,601 B2 | 11/2006 | Bucholz et al. | |
| 7,179,261 B2 | 2/2007 | Sicvol et al. | |
| 7,559,931 B2 | 7/2009 | Stone | |
| 7,611,522 B2 | 11/2009 | Gorek | |
| 7,634,119 B2 | 12/2009 | Tsougarakis et al. | |
| 7,666,188 B2 | 2/2010 | Anderson et al. | |
| 7,706,000 B2 | 4/2010 | Cohen | |
| 7,918,887 B2 | 4/2011 | Roche | |
| 7,955,355 B2 | 6/2011 | Chin | |
| 7,956,887 B2 | 6/2011 | Hoeg et al. | |
| 7,957,809 B2 | 6/2011 | Bourget et al. | |
| 7,981,115 B2 | 7/2011 | Justis et al. | |
| 8,057,479 B2 | 11/2011 | Stone | |
| 8,057,482 B2 | 11/2011 | Stone et al. | |
| 8,128,662 B2 | 3/2012 | Altarac et al. | |
| 8,167,823 B2 | 5/2012 | Nycz et al. | |
| 8,442,621 B2 | 5/2013 | Gorek et al. | |
| 8,549,888 B2 | 10/2013 | Isaacs | |
| 8,565,853 B2 | 10/2013 | Frigg et al. | |
| 8,690,888 B2 | 4/2014 | Stein et al. | |
| 8,888,821 B2 | 11/2014 | Rezach et al. | |
| 8,906,034 B2 | 12/2014 | Gleeson et al. | |
| 9,241,742 B2 | 1/2016 | Stad | |
| 9,999,448 B2 | 6/2018 | Stad | |
| 2002/0035321 A1 | 3/2002 | Bucholz et al. | |
| 2004/0102781 A1 | 5/2004 | Jeon | |
| 2004/0138662 A1 | 7/2004 | Landry et al. | |
| 2004/0143178 A1 | 7/2004 | Leitner et al. | |
| 2004/0220567 A1 | 11/2004 | Eisermann et al. | |
| 2005/0085714 A1 | 4/2005 | Foley et al. | |
| 2005/0222793 A1 | 10/2005 | Lloyd et al. | |
| 2005/0262911 A1 | 12/2005 | Dankowicz et al. | |
| 2006/0009780 A1 | 1/2006 | Foley et al. | |
| 2006/0200130 A1 | 9/2006 | Hawkins et al. | |
| 2006/0200132 A1 | 9/2006 | Chao et al. | |
| 2006/0247773 A1 | 11/2006 | Stamp | |
| 2006/0264962 A1 | 11/2006 | Chin et al. | |
| 2006/0271050 A1 | 11/2006 | Piza Vallespir | |
| 2007/0043379 A1 | 2/2007 | Sullivan et al. | |
| 2007/0093817 A1 | 4/2007 | Barrus et al. | |
| 2008/0077138 A1 | 3/2008 | Cohen et al. | |
| 2008/0177203 A1 | 7/2008 | von Jako | |
| 2008/0228195 A1 | 9/2008 | von Jako et al. | |
| 2008/0292161 A1 | 11/2008 | Funk et al. | |
| 2008/0294206 A1 | 11/2008 | Choi et al. | |
| 2009/0171391 A1* | 7/2009 | Hutton | A61B 17/7032 606/246 |
| 2009/0249851 A1 | 10/2009 | Isaacs | |
| 2010/0010494 A1 | 1/2010 | Quimo | |
| 2010/0036384 A1 | 2/2010 | Gorek et al. | |
| 2010/0069919 A1 | 3/2010 | Carls et al. | |
| 2010/0087823 A1 | 4/2010 | Kondrashov | |
| 2010/0100011 A1 | 4/2010 | Roche | |
| 2010/0312103 A1 | 12/2010 | Gorek et al. | |
| 2011/0040340 A1 | 2/2011 | Miller et al. | |
| 2011/0077689 A1 | 3/2011 | Mickiewicz et al. | |
| 2011/0106082 A1 | 5/2011 | Kaye et al. | |
| 2011/0125196 A1 | 5/2011 | Quevedo et al. | |
| 2011/0270262 A1 | 11/2011 | Justis et al. | |
| 2011/0275957 A1 | 11/2011 | Bhandari | |
| 2011/0295159 A1 | 12/2011 | Shachar et al. | |
| 2011/0319938 A1 | 12/2011 | Piza Vallespir et al. | |
| 2012/0071885 A1 | 3/2012 | Forton et al. | |
| 2012/0197297 A1 | 8/2012 | Bootwala et al. | |
| 2013/0072982 A1* | 3/2013 | Simonson | A61B 17/7083 606/267 |
| 2013/0268007 A1 | 10/2013 | Rezach et al. | |
| 2014/0052149 A1 | 2/2014 | van der Walt et al. | |
| 2014/0057572 A1 | 2/2014 | Klinghult et al. | |
| 2014/0088607 A1 | 3/2014 | Recknor | |
| 2014/0171965 A1 | 6/2014 | Loh et al. | |
| 2014/0275981 A1 | 9/2014 | Selover et al. | |
| 2014/0277198 A1 | 9/2014 | Stad | |
| 2015/0305786 A1 | 10/2015 | Wehrle et al. | |
| 2016/0095631 A1 | 4/2016 | Stad | |
| 2016/0360997 A1 | 12/2016 | Yadav et al. | |
| 2017/0196507 A1 | 7/2017 | Singh et al. | |
| 2019/0090955 A1 | 3/2019 | Singh et al. | |

FOREIGN PATENT DOCUMENTS

| | | |
|---|---|---|
| WO | 2005/077000 A2 | 8/2005 |
| WO | 2013/053398 A1 | 4/2013 |
| WO | 2013/169674 A1 | 11/2013 |
| WO | 2014/063181 A1 | 5/2014 |
| WO | 2015/003224 A1 | 1/2015 |
| WO | 2015/114119 A1 | 8/2015 |

OTHER PUBLICATIONS

[No Author Listed] Viper 2 MIS Spine System, System Guide. DePuy Spine Inc. Sep. 2011. 60 pages.

Delorme, et al., Intraoperative comparison of two instrumentation techniques for the correction of adolescent idiopathic scoliosis. Rod rotation and translation. Spine (Phila Pa 1976). Oct. 1, 1999;24(19)2011-7.

*Ghanem, et al., Intraoperative optoelectronic analysis of three-dimensional vertebral displacement after Cotrel-Dubousset rod rotation. A preliminary report. Spine (Phila Pa 1976). Aug. 15, 1997;22(16):1913-21.

Lafon, et al., Intraoperative three-dimensional correction during rod rotation technique. Spine (Phila Pa 1976). Mar. 1, 2009;34(5):512-9. doi: 10.1097/BRS.0b013e31819413ec.

Lafon, et al., Intraoperative three dimensional correction during in situ contouring surgery by using a numerical model. Spine (Phila Pa 1976). Feb. 15, 2010;35(4):453-9. doi: 10.1097/BRS.0b013e3181b8eaca. Abstract.

Luc Duong, et al., Real time noninvasive assessment of external trunk geometry during surgical correction of adolescent idiopathic scoliosis. Scoliosis. Feb. 24, 2009;4:5. doi: 10.1186/1748-7161-4-5.

Mac-Thiong, et al., A new technique for intraoperative analysis of trunk geometry in adolescent idiopathic scoliosis. Can J Surg. Jun. 2002;45(3):219-23.

(56) References Cited

OTHER PUBLICATIONS

Mac-Thiong, et al., The effect of intraoperative traction during posterior spinal instrumentation and fusion for adolescent idiopathic scoliosis. Spine (Phila Pa 1976). Jul. 15, 2004;29(14):1549-54.

* cited by examiner

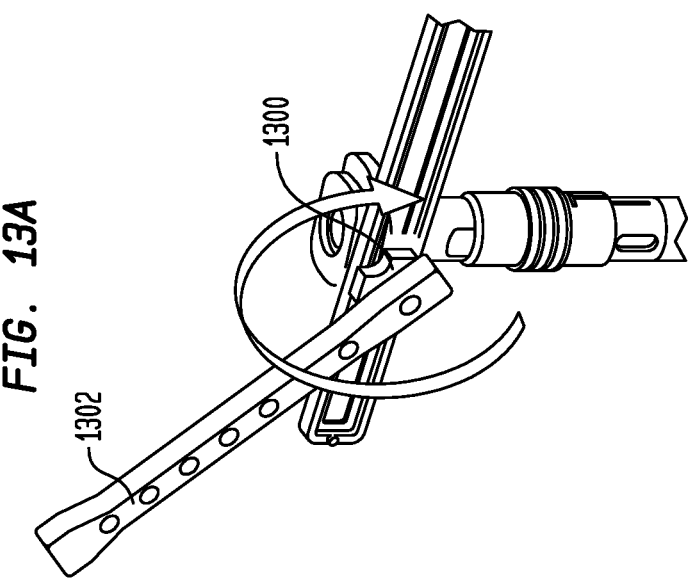
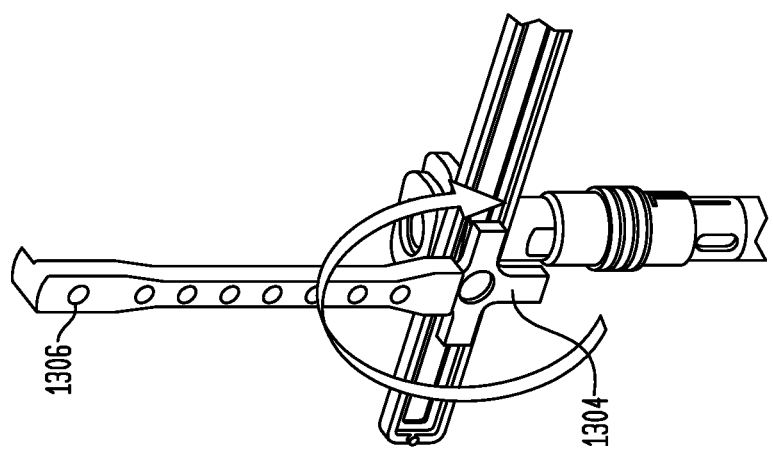
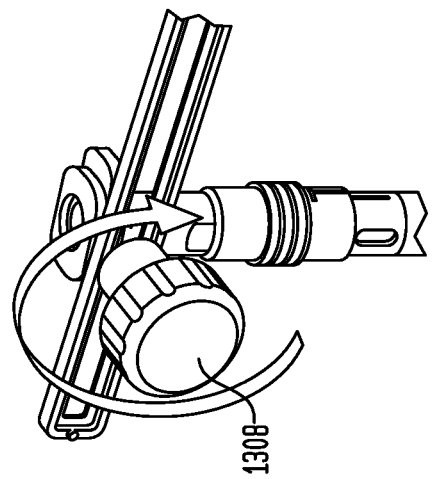

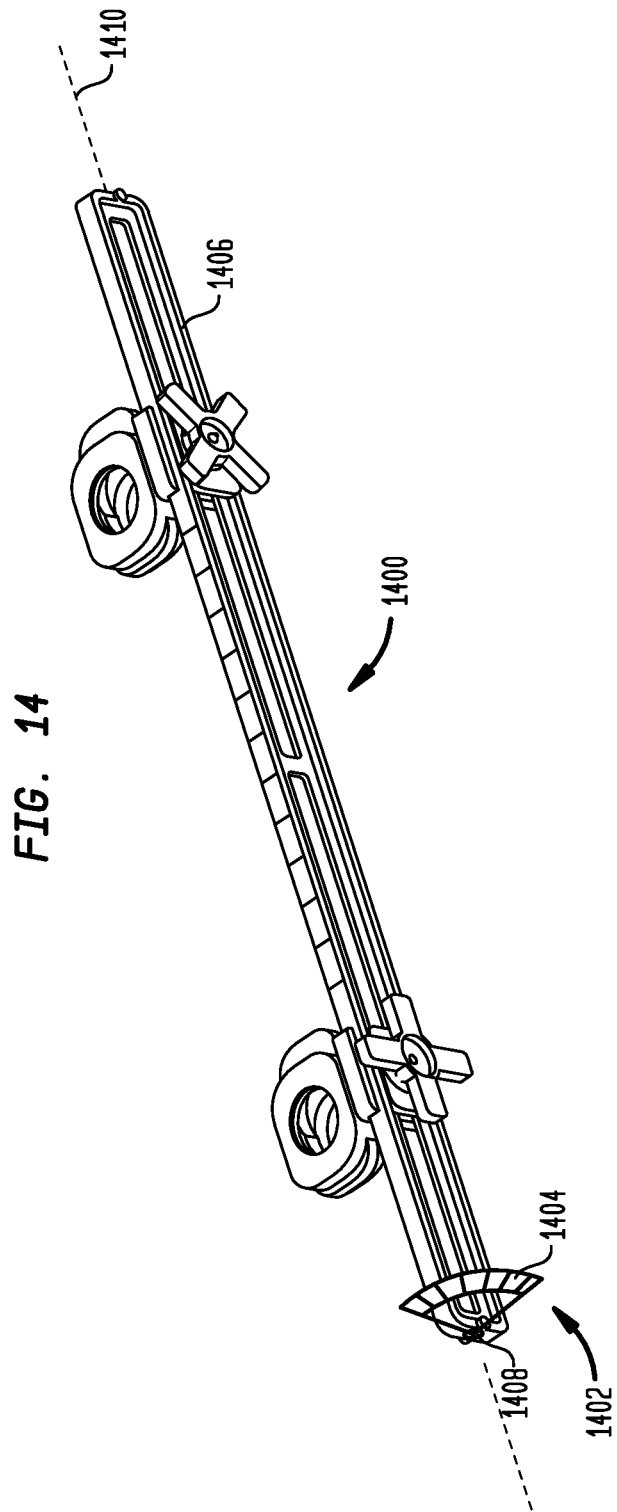

METHODS AND DEVICES FOR POLYAXIAL SCREW ALIGNMENT

CROSS-REFERENCE TO RELATED APPLICATIONS

This application is a continuation of U.S. patent application Ser. No. 14/961,065 filed on Dec. 7, 2015 entitled "METHODS AND DEVICES FOR POLYAXIAL SCREW ALIGNMENT," and now issued as U.S. Pat. No. 9,999,448. U.S. patent application Ser. No. 14/961,065 is a continuation of U.S. patent application Ser. No. 13/830,548 filed on Mar. 14, 2013, entitled "METHODS AND DEVICES FOR POLYAXIAL SCREW ALIGNMENT," and now issued as U.S. Pat. No. 9,241,742. Each of these applications is hereby incorporated by reference in its entirety.

FIELD

The present invention relates to methods and devices for use in spinal surgery, and in particular to instruments and methods for use during spinal fixation procedures.

BACKGROUND

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. Alternatively, two rods can be disposed on the lateral or anterior surface of the vertebral body in a substantially parallel relationship. The fixation rods can have a predetermined contour that has been designed according to the properties of the target implantation site and, once installed, the rods hold the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a receiving member having a U-shaped slot for seating the fixation rod. The receiving member can be monoaxial and thus fixed relative to the threaded shank, or it can be polyaxial and thus movable relative to the threaded shank. Polyaxial screws can facilitate positioning of the fixation rod therein. Extension members are often coupled to the receiving member, especially in minimally invasive procedures, to provide a pathway through tissue to the receiving member. A set-screw, plug, or similar type of closure mechanism, is used to lock the fixation rod into the rod receiving member of the pedicle screw.

While current spinal fixation systems have proven effective, difficulties are still encountered in various spinal procedures, such as when correcting spinal deformities. For example, the use of polyaxial screws in these operations can aid in capturing a rod or other spinal fixation element within the receiving member of the polyaxial screw due to the ability of the receiving member to move relative to the threaded shank implanted in the patient's vertebra. However, the movement provided by polyaxial screws can limit a surgeon's control when applying corrective forces to the screw in order to effect movement of the vertebra. Various devices exist to lock a polyaxial screw in a monoaxial configuration, but these devices can be problematic as well because surgeons often cannot tell when the receiving member is correctly oriented with respect to the threaded shank implanted within the vertebra. In particular, locking the polyaxial screw in a monoaxial configuration when the receiving member is angled relative to the threaded shank can create large moment forces on the screw during the application of corrective forces. To combat these forces, surgeons often want to lock the polyaxial screw in a monoaxial configuration when the receiving member is aligned with the threaded shank (i.e., the longitudinal axes of the receiving member and the threaded shank are coaxial). Because there is not an easy and cost-effective way to align a polyaxial screw in a coaxial configuration, surgeons often utilize various combinations of polyaxial, monoaxial, and uniplanar screws (the latter provides relative motion between the receiving member and threaded shank in only a single plane).

The use of multiple screw types, however, can be problematic because they add to the complexity of an already technically challenging procedure. Furthermore, beyond the addition of the screws themselves, the use of additional screw types can require that additional instrumentation be present in the operating room as well. Surgeons may need additional training on the use of the different screw types and their associated instrumentation, and costs associated with sterilizing and maintaining the instrumentation and implants are also increased. Still further, monoaxial and, to a lesser degree, uniplanar screws lack the ability to conform to a rod or other spinal fixation element, which can increase the difficulty of capturing and approximating a rod or other spinal fixation element during a procedure.

Accordingly, there is a need in the art for methods and devices that allow surgeons to utilize polyaxial screws in a wider range of surgical procedures. In particular, there is a need for methods and devices that allow for rod capture via polyaxial movement of a screw receiving member while also allowing a surgeon to selectively lock the receiving member in coaxial alignment with an implanted shank after rod capture.

SUMMARY

The present invention generally provides methods and devices for polyaxial screw alignment that allow surgeons to position the components of one or more polyaxial screws in a coaxial orientation at any point in the procedure. The methods and devices described herein generally involve recording and/or capturing the orientation of one or more polyaxial screws after implantation and prior to rod capture when an alignment device can be coupled to both the receiving member and the threaded shank of a polyaxial screw to ensure that the two are in coaxial alignment. The deformity correction or other spinal procedure can then proceed as usual, and a surgeon can later return the one or more polyaxial screws to a coaxial orientation despite the fact that the alignment shaft can no longer be used due to the presence of a spinal fixation rod or other element in the receiving member of the one or more screws.

The orientation of the one or more screws can be captured using a variety of devices and methods. In some embodiments, for example, an elongate frame can be coupled to the one or more polyaxial screws and selectively locked to maintain their relative position and orientation in a plane extending along a longitudinal axis of the frame. Furthermore, the frame can include a transverse angle indicator configured to indicate an angular orientation of the frame in a plane transverse to the longitudinal axis of the frame. By coupling the elongate frame to the one or more polyaxial screws when the alignment shaft is present and subsequently matching the orientation of the one or more screws to the elongate frame at a later time when the alignment shaft is not present, a surgeon can be sure that the one or more polyaxial screws have been returned to a coaxial orientation.

In other embodiments, an image guidance system (IGS) or some other precision positioning system can be used in place of a locking frame. Regardless, the procedure entails recording and/or capturing the position and orientation of one or more polyaxial screws when an alignment shaft is present in the screw to ensure its alignment, and then guiding a surgeon to return the polyaxial screw to the coaxially aligned orientation at a later time when the alignment shaft is not present.

In one aspect, a polyaxial screw alignment instrument is provided that includes an elongate frame having a longitudinal axis extending therethrough, and a plurality of connection caps slidably disposed along the elongate frame. Each connection cap can be configured to removably couple to a polyaxial screw extension tube and to selectively lock relative to the elongate frame such that a distance between the plurality of connection caps and an angular orientation of each connection cap relative to the elongate frame can be maintained. The alignment instrument can further include a transverse angle indicator configured to indicate an angular orientation of the elongate frame in a plane transverse to the longitudinal axis of the elongate frame.

The methods and devices described herein can include a number of additional features and/or variations, all of which are considered within the scope of the present invention. For example, in some embodiments the plane in which the transverse angle indicator measures an angular orientation is perpendicular to the longitudinal axis of the elongate frame. In other embodiments, the plane in which the transverse angle indicator measures an angular orientation can be offset by some other angle from the longitudinal axis of the elongate frame. Furthermore, in some embodiments, the elongate frame can be configured to measure the angular orientation and distance between a plurality of polyaxial screws in the transverse plane of the body, and the transverse angle indicator can be configured to measure the angular orientation of the elongate frame in the sagittal plane of the body, as described in more detail below.

A number of different mechanical devices can be employed as the transverse angle indicator. For example, in some embodiments, the transverse angle indicator can include a bubble level coupled to the elongate frame. The bubble level can be, for example, rotatably coupled to the frame such that it can be rotated to a level position to mark the angular orientation of the elongate frame. In other embodiments, the transverse angle indicator can include an angular scale coupled to the elongate frame. The angular scale can, in some embodiments, also be rotatably coupled to the elongate frame such that a user can align an edge of the frame with the vertical or horizontal and read off the angular orientation of the elongate frame. Alternatively, the scale can be rigidly coupled to the elongate frame and utilize a hanging plumb line or other method known in the art to indicate the angular orientation of the elongate frame. In still other embodiments, the transverse angle indicator can include an arm coupled to the elongate frame and an operating surface. The arm can be adjustable and can serve to couple the frame to a fixed frame of reference, such as the operating surface. The angular orientation of the arm can be captured or maintained with respect to the operating surface. In other embodiments, a surface other than the operating surface can be utilized, so long as it provides a fixed frame of reference for anchoring the adjustable arm.

In other embodiments, each of the plurality of connection caps can include a thumbscrew configured to selectively lock the connection cap relative to the elongate frame when tightened. For example, the thumbscrew can be loosened to allow the connection cap to slide along the elongate frame and rotate relative thereto, but upon tightening can rigidly fix the connection cap to the elongate frame such that it does not slide or rotate.

In another aspect, a polyaxial screw alignment system is provided that includes a plurality of polyaxial screws having a threaded shank and a receiving member coupled to the threaded shank that can move polyaxially with respect to the threaded shank. The system can further include a plurality of extension tubes, each extension tube configured to be coupled to the receiving member of one of the plurality of polyaxial screws such that a longitudinal axis of the extension tube and a longitudinal axis of the receiving member are maintained in a coaxial orientation. The system can also include a plurality of alignment shafts, each alignment shaft configured to be coupled to one of the plurality of polyaxial screws such that a longitudinal axis of the threaded shank and a longitudinal axis of the receiving member are maintained in a coaxial orientation. The system can further include a polyaxial screw alignment instrument having an elongate frame and a plurality of connection caps slidably disposed thereon, each connection cap configured to be coupled to a proximal end of one of the plurality of extension tubes and selectively locked relative to the elongate frame to maintain a distance between the plurality of connection caps and an angular orientation of each of the connection caps relative to the elongate frame, as well as a transverse angle indicator that indicates an angular orientation of the elongate frame of the polyaxial screw alignment instrument in a plane transverse to a longitudinal axis of the elongate frame.

In some embodiments, the transverse angle indicator can include a bubble level coupled to the elongate frame. In other embodiments, however, the transverse angle indicator can include an angular scale coupled to the elongate frame. In still other embodiments, the transverse angle indicator can include an arm coupled to the elongate frame and an operating surface.

In certain embodiments, each of the plurality of alignment shafts can threadably engage with the receiving member of one of the plurality of polyaxial screws. The threaded interface between the receiving member and the alignment shaft can ensure that a longitudinal axis of the receiving member is coaxially aligned with a longitudinal axis of the alignment shaft. Moreover, in some embodiments, each of the plurality of alignment shafts can include a protrusion formed on a distal end thereof that interfaces with a recess formed in the threaded shank of the polyaxial screw. For example, the alignment shaft can be a single-piece member and the protrusion can include a feature that is accepted within a recess formed at the proximal end of the threaded shank to allow the alignment shaft to rotate the threaded shank. The interface of the protrusion of the alignment shaft and the recess of the threaded shank can ensure that a longitudinal axis of the threaded shank is coaxially aligned with a longitudinal axis of the alignment shaft. In another embodiment, the alignment shaft can be a two-piece member, which assists in coaxial alignment and also enables driving of the threaded shank. In the two-piece embodiment the shaft and external threads are similar to the one-piece embodiment except that a lumen extends longitudinally through the shaft and the distal end, which includes the external threads. The two-piece embodiment further includes, as a second and separate component, an elongate drive member that is configured to be passed through the lumen so as to extend beyond the distal end of the threaded shaft to engage the recess of the threaded shank. The separate drive member can be manipulated independently of the threaded shaft, e.g., such as to rotate and drive the threaded shank.

In another aspect, a method of aligning polyaxial screws is provided that includes coupling a plurality of extension tubes to receiving members of a plurality of polyaxial screws, and coupling a plurality of alignment shafts to the plurality of polyaxial screws such that each alignment shaft maintains a longitudinal axis of a receiving member and a longitudinal axis of a threaded shank of one of the plurality of polyaxial screws in a coaxial orientation. The method can further include coupling a polyaxial screw alignment instrument to proximal ends of the plurality of extension tubes and selectively locking the polyaxial screw alignment instrument to indicate a distance between and an angular orientation of each of the plurality of extension tubes relative to a longitudinal axis of the polyaxial screw alignment instrument. The method can also include indicating an angular orientation of the polyaxial screw alignment instrument in a plane transverse to the longitudinal axis of the polyaxial screw alignment instrument.

In certain embodiments, the method can also include removing the polyaxial screw alignment instrument from the proximal ends of the plurality of extension tubes, and removing the plurality of alignment shafts from the plurality of polyaxial screws. Still further, the method can include passing a spinal fixation element through the receiving member of at least one of the plurality of polyaxial screws, and re-coupling the polyaxial screw alignment instrument to the proximal ends of the plurality of extension tubes to return each of the plurality of polyaxial screws to an orientation wherein a longitudinal axis of the receiving member and a longitudinal axis of the threaded shank are coaxial.

In some embodiments, the method can include inserting a set screw into each of the plurality of polyaxial screws after re-coupling the polyaxial screw alignment instrument to maintain the coaxial orientation of the receiving member and the threaded shank. The set screw is one example of a closure mechanism that can be used to temporarily or permanently secure the orientation of the polyaxial screw, as well as its position and orientation with respect to a spinal fixation element such as a rod, plate, etc.

In certain embodiments, the plurality of polyaxial screws can include two polyaxial screws implanted bilaterally in a patient's vertebra. Surgeons often work on a single vertebral level at a time, or on a single vertebra and its closest adjacent vertebra. Accordingly, the polyaxial screw alignment instruments described herein can be particularly suited to capturing the orientation of neighboring polyaxial screws implanted bilaterally in a single vertebra of a patient. In other embodiments, however, the polyaxial screw alignment instruments described herein can be used in alternative locations, including, for example, in capturing the orientation of a plurality of polyaxial screws extending across a plurality of vertebral levels on one side of the spine.

In another aspect, a method of aligning polyaxial screws is provided that includes coupling an extension tube to a receiving member of a polyaxial screw where the extension tube includes features recognizable to a surgical image guidance system. The method can further include coupling an alignment shaft to the polyaxial screw such that the alignment shaft can maintain a longitudinal axis of the receiving member and a longitudinal axis of a threaded shank of the polyaxial screw in a coaxial orientation, as well as measuring the three-dimensional position and angular orientation of the extension tube using the surgical image guidance system.

In some embodiments, the method can also include removing the alignment shaft from the polyaxial screw after measuring the three-dimensional position and angular orientation of the extension tube, and passing a spinal fixation element through the receiving member of the polyaxial screw. The method can further include measuring the three-dimensional position and angular orientation of the extension tube using the surgical image guidance system a second time, as well as adjusting the extension tube to place the longitudinal axis of the receiving member and the longitudinal axis of the threaded shank in a coaxial orientation based on guidance from the surgical image guidance system.

In other embodiments, the method can further include inserting a set screw into the polyaxial screw after adjusting the extension tube to maintain the coaxial orientation of the receiving member and the threaded shank. As described above, in some embodiments, the polyaxial screw can be implanted in a patient's vertebra.

BRIEF DESCRIPTION OF THE DRAWINGS

The aspects and embodiments of the invention described above will be more fully understood from the following detailed description taken in conjunction with the accompanying drawings, in which:

FIG. 13A illustrates one embodiment of a selective locking mechanism of a polyaxial screw alignment instrument;

FIG. 13B illustrates an alternative embodiment of a selective locking mechanism of a polyaxial screw alignment instrument;

FIG. 13C illustrates an alternative embodiment of a selective locking mechanism of a polyaxial screw alignment instrument;

FIG. 14 is a perspective view of an alternative embodiment of a polyaxial screw alignment instrument;

DETAILED DESCRIPTION

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention is generally directed to devices and methods for polyaxial screw alignment. More particularly, the methods and devices described herein can allow a surgeon to reliably position one or more polyaxial screws in an orientation that coaxially aligns a longitudinal axis of a receiving member and a longitudinal axis of a threaded shank of each screw. This can be advantageous because surgeons often desire polyaxial movement of a receiving member relative to a threaded shank during certain stages of spinal surgery (e.g., rod capture), but want monoaxial rigidity and control during other stages (e.g., deformity correction, distraction, compression, etc.). Furthermore, locking a polyaxial screw in an orientation in which the longitudinal axes of the receiving member and the threaded shank are angularly offset can subject the screw to large or misdirected moment forces when corrective forces are applied. Using prior art devices and methods, however, there is not a reliable and effective way to determine when the components of a polyaxial screw are in coaxial alignment, especially after a rod or other spinal fixation element has been seated within the receiving member of the screw. The devices and methods described herein address this shortcoming by capturing the orientation of one or more polyaxial screws when their coaxial alignment can be ensured (e.g., prior to rod capture) and allowing a user to easily return the screw to that same orientation at a later point in the procedure (e.g., after rod capture).

Figure 1:
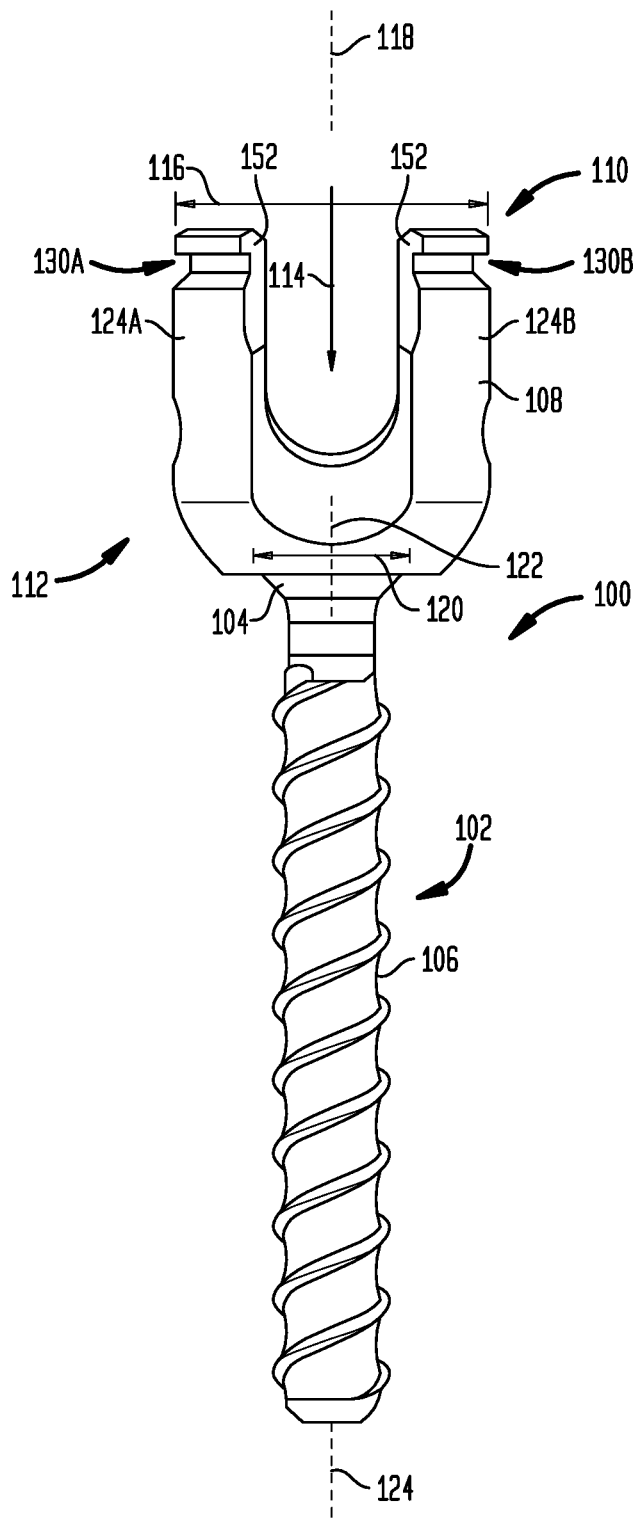
FIG. 1 is a front view of a prior art polyaxial bone screw.

FIG. 1 illustrates one embodiment of a polyaxial screw 100 known in the art. The polyaxial screw 100 includes a bone anchor 102, such as a pedicle screw, having a proximal head 104 and a distal bone-engaging portion 106, which in the illustrated exemplary embodiment is an externally threaded screw shank. The polyaxial screw 100 also includes a receiving member 108 that is configured to receive and couple a spinal fixation element, such as a spinal rod or spinal plate, to the polyaxial screw 100.

The receiving member 108 may be coupled to the bone anchor 102 in any manner known in the art. For example, the bone anchor 102 may be adjustable to multiple angles relative to the receiving member 108. This is in contrast to monoaxial bone screws, in which the bone anchor 102 and the receiving member 108 are not movable relative to one another. An exemplary polyaxial bone screw is described U.S. Pat. No. 5,672,176, which is herein incorporated by reference in its entirety.

The receiving member 108 of the illustrated exemplary embodiment includes a proximal end 110, a distal end 112, and a recess or slot 114 for receiving a spinal fixation element, such as a spinal rod. The proximal end 110 of the receiving member 108 has a first bore 116 formed therein that defines a first bore axis 118 and communicates with the recess 114 such that a spinal fixation element may be positioned through the first bore into the recess 114. The first bore axis 118 can be considered the longitudinal axis of the receiving member 108. The distal end 112 has a second bore 120 opposite the first bore 116 that defines a second bore axis 122 and is designed to receive the head 104 of the bone anchor 102 to couple the bone anchor to the receiving member 108. In the illustrated exemplary embodiment, the head 104 is seated within the second bore 120. As the exemplary illustrated embodiment of the bone anchor assembly is polyaxial, the bone anchor 102 is free to rotate relative to the receiving member 108 such that the longitudinal axis 124 of the bone anchor 102 is positionable at an angle relative to the second bore axis 122 of the receiving member 108 (in FIG. 1, the first bore axis 118, second bore axis 122, and longitudinal axis 124 of the bone anchor 102 are coaxial). The second bore 120 may be spherically or conically shaped to facilitate adjustment of the bone anchor 102 relative to the receiving member 108. In the exemplary embodiment, the receiving member 108 has a generally U-shaped cross-section defined by two legs 124A and 124B separated by recess 114. Each leg 124A, 124B is free at the proximal end 110 of the receiving member 108.

The receiving member 108 may be configured to receive a closure mechanism that locks a spinal fixation element within the recess 114. The closure mechanism may be a cap that is advanceable through the first bore 116 of the receiving member 108 and seats against the spinal fixation element. For example, the cap may have external threads that engage internal threads provided in the receiving member 108, e.g., on the legs 124A, 124B. Any type of conventional closure mechanism may be employed, including, for example, non-threaded caps, multi-component closure mechanisms, and/or external caps.

The receiving member 108 of the exemplary polyaxial screw 100 can include features allowing it to be releasably connected to a variety of instruments, such as the polyaxial screw extension tube described below. For example, the receiving member 108 may include at least one groove that is configured to receive a portion of an instrument to releasably connect the instrument to the polyaxial screw.

The size, shape, position, and number of grooves can be varied depending on, for example, the instrument employed and the type of connection desired. In certain embodiments, for example, at least one arcuate groove may be provided on an exterior surface of the proximal end 110 of the receiving member 108. In other exemplary embodiments, at least one arcuate groove may be provided on an interior surface of the proximal end 110 of the receiving member 108. In the illustrated exemplary embodiment, each leg 124A and 124B may be provided with an arcuate groove 130A, 130B, respectively, at the free, proximal end of the leg 124A, 124B. The grooves 130A, 130B may extend about a portion or the entirety of the circumference of the proximal end of each leg 124A, 124B. Each groove 130A, 130B may have a size and shape that is complementary in size and shape to a projection or other feature provided on the instrument, as described in more detail below.

Figure 2:
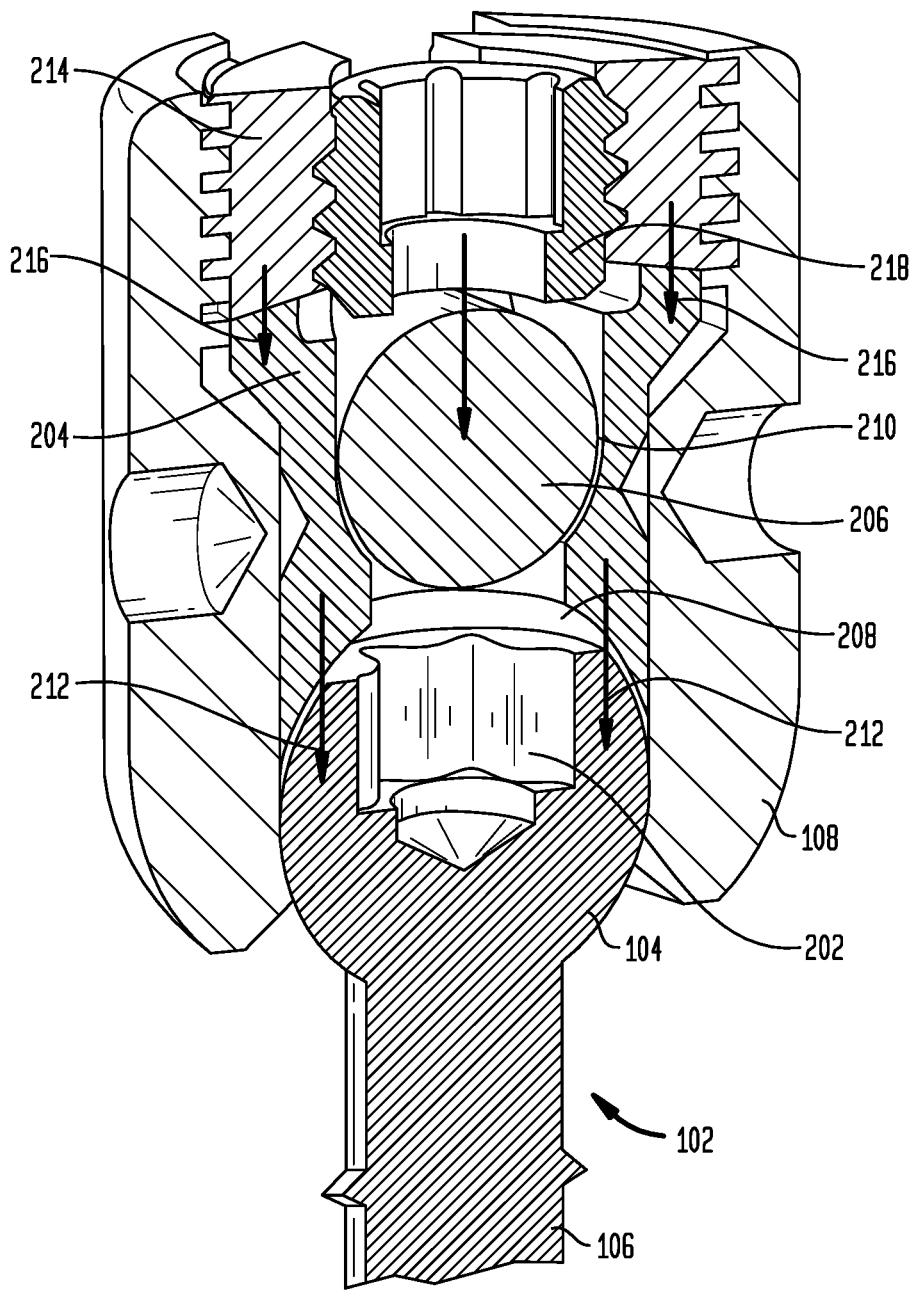
FIG. 2 is a cross-sectional view of another version of a prior art polyaxial screw.

FIG. 2 illustrates the polyaxial screw 100 in cross-section. In particular, the spherical head 104 of the bone anchor 102 is shown extending through the second bore 120 formed in the distal end of the receiving member 108 and seated within a spherical seat in the receiving member. The head 104 can include a recess 202 or other feature that can receive a driver or other instrument, such as the alignment shaft described below. Also shown is a compression member 204 that resides within the recess 114 of the receiving member 108. The compression member 204 can include an inner lumen that allows a driver or other instrument to access the recess 202 of the bone anchor 102. Furthermore, the compression member 204 can include features formed at its proximal and distal ends that are configured to interface with a spinal fixation element, such as the spinal fixation rod 206, and the head 104 of the bone anchor 102, respectively. For example, the compression member 204 can include a hemispherical recess 208 formed at its distal end that can mirror the shape of the head 104 of the bone anchor 102. At its proximal end, the compression member 204 can include a U-shaped recess 210 that is configured to seat a spinal fixation element, such as the spinal fixation rod 206.

The compression member 204 can be configured to travel within the recess 114 of the receiving member 108 along the first bore axis 118 between a first position in which the compression member allows polyaxial movement of the head 104 within the receiving member 108 and a second position (shown by arrows 212 in FIG. 2) in which the compression member locks the orientation of the bone anchor 102 with respect to the receiving member 108. This is typically accomplished with the use of a closure mechanism, such as the outer set screw 214. As the outer set screw 214 is threaded into the proximal end of the receiving member 108, it can exert a downward force on the compression member 204 (shown by arrows 216 in FIG. 2), thereby pushing the compression member 204 from the first position to the second position and locking the orientation of the bone anchor 102 and the receiving member. The outer set screw 214 can itself include an inner lumen to receive an inner set screw 218 that can be used to lock the receiving member in a particular orientation and position along the spinal fixation rod 206 by pressing the rod into the U-shaped recess 210 of the compression member (shown by arrows 216 in FIG. 2).

Figure 3:
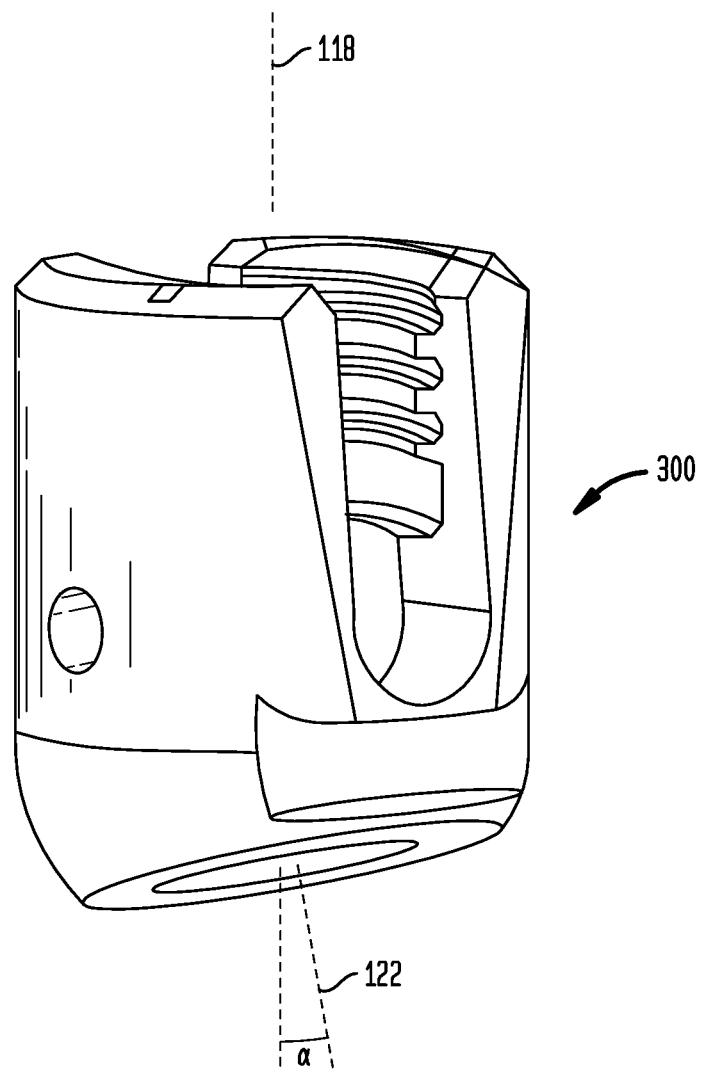
FIG. 3 is a perspective view of an alternative embodiment of a prior art receiving member of a polyaxial screw.

There are a number of variations on the polyaxial screw 100 known in the art. For example, FIG. 3 illustrates an embodiment of a polyaxial screw receiving member 300 that is biased to a particular angle or range of angles to provide a favored angle to the bone anchor 102. This favored angle can aid in rod capture during a spinal procedure as the receiving member 108 can have additional range of motion in one direction, e.g., laterally away from the spinal column. In favored angle embodiments, the second bore axis 122 can be positioned at an angle α (other than 0°) to the first bore axis 118. Exemplary favored angle bone screws are described in U.S. Pat. Nos. 6,736,820 and 6,974,460, both of which are herein incorporated by reference in their entirety.

Figure 4:
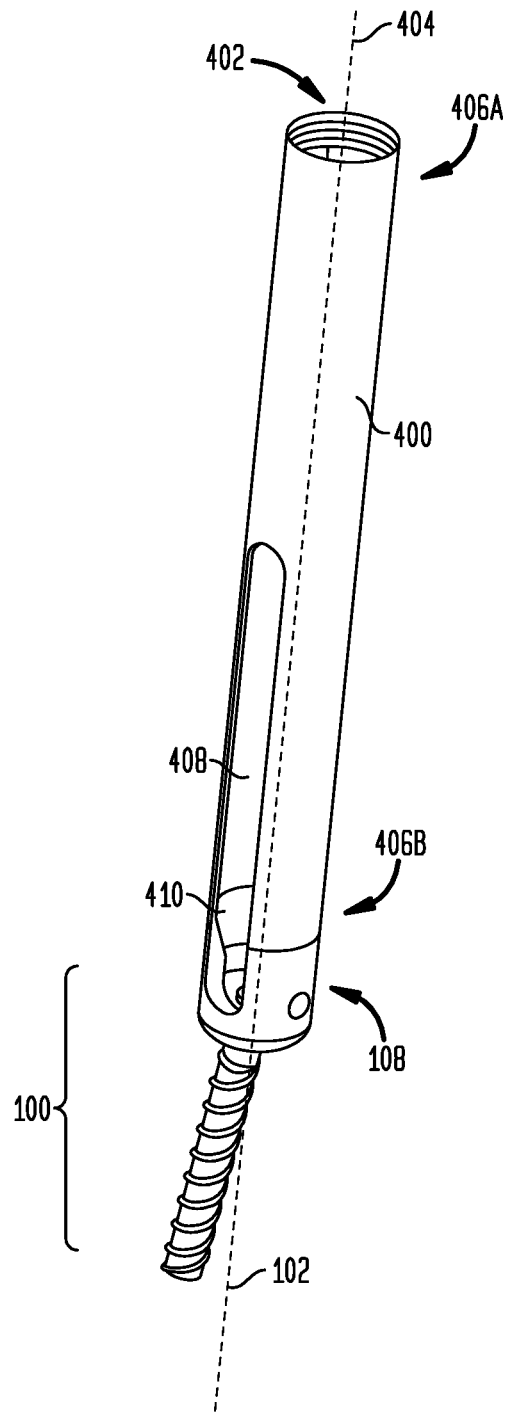
FIG. 4 is a perspective view of a prior art polyaxial screw extension tube coupled to the polyaxial screw of FIG. 1.
Figure 5:
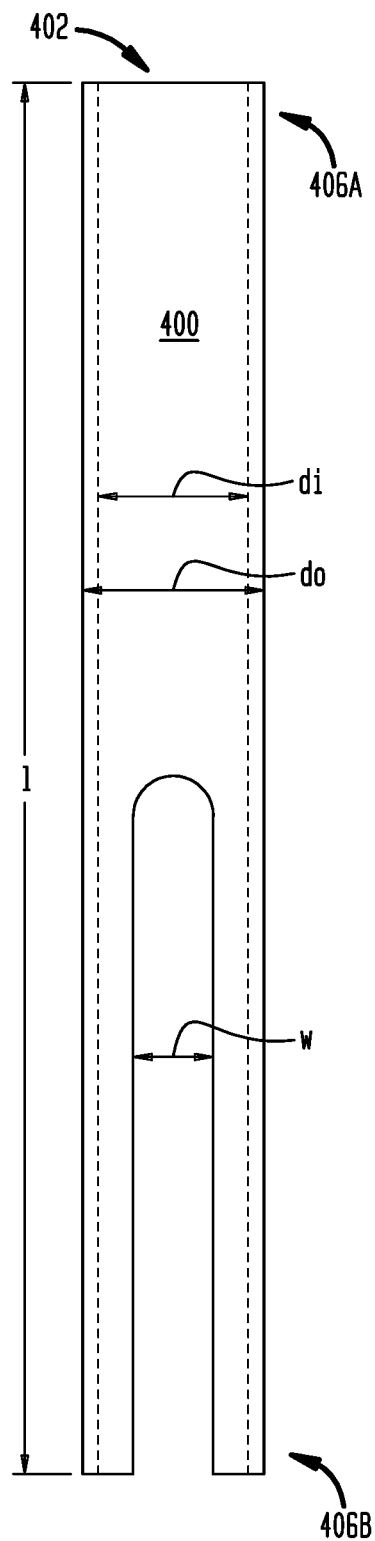
FIG. 5 is a front view of the prior art polyaxial screw extension tube of FIG. 4.

The receiving member 108 can be configured to couple with a variety of instruments, as described above. FIGS. 4-5 illustrate one embodiment of such an instrument known as a polyaxial screw extension tube. The extension tube 400 is in the form of a generally elongate, cylindrical tube having an inner lumen 402 formed therein and defining a longitudinal axis 404 that extends between proximal and distal ends 406A, 406B. The size of the extension tube 400 can vary depending on intended use, but it should have a length l that allows the proximal end 406A of the extension tube 400 to be positioned outside a patient's body while the distal end 406B of is coupled to the receiving member 108 of the polyaxial screw 100 that is implanted in a patient's spine. As a result, the extension tube 400 can provide a more readily accessible component that can be manipulated by a surgeon or other tool to impart correctional forces to the polyaxial screw 100 and the vertebra in which it is implanted. Further, the inner diameter $d_i$ of the extension tube 400 be sufficiently large to accommodate a diameter or width of a spinal fixation element, closure mechanism, or other tool (e.g., the alignment shaft described below) to be introduced therethrough to access the polyaxial screw.

The extension tube 400 can, in some embodiments, optionally include at least one sidewall opening or slot 408 formed therein and extending proximally from the distal end 406B thereof. A person of skill in the art will understand that such sidewall openings or slots are not necessary in some embodiments. The openings 408 can allow a spinal fixation element to be positioned lengthwise between two adjacent polyaxial screws 100 and attached extension tubes 400 such that the spinal fixation element extends in an orientation that is substantially transverse to the longitudinal axis 404 of the extension tube 400, i.e., that crosses the longitudinal axis 404 of the extension tube 400. The exact position of the spinal fixation element with respect to the longitudinal axis 404 will of course vary depending on the configuration of the spinal fixation element. The shape and size of the openings 408 can also vary depending on the configuration of the spinal fixation element, but the openings 408 can have a generally elongate shape with a width w that is sufficient to accommodate the diameter of the spinal fixation element. The openings 408 can extend over any length of the extension tube 400. In some embodiments, the openings 408 can extend such that a proximal portion of each opening 408 is positioned outside a patient's body while the extension tube 400 is in use, thus allowing a spinal fixation element to be externally positioned through the openings 408 and then moved distally to be implanted.

Continuing to refer to FIGS. 4-5, in use, the extension tube 400 can be adapted to attach to the receiving member 108 of the polyaxial screw 100. Accordingly, the distal end 406B of the extension tube 400 can include one or more mating elements 410 formed thereon or therein for engaging the receiving member 108. Suitable mating elements include, for example, threads, a twist-lock engagement, a snap-on engagement, or any other technique known in the art, and in an exemplary embodiment the mating elements can be formed on opposed inner surfaces of the distal end 406B of the extension tube 400. In some embodiments, the mating elements 410 can be configured to couple the extension tube 400 to the receiving member 108 such that the longitudinal axis 404 of the extension tube 400 is coaxial with the longitudinal axis 118 of the receiving member 108. A sleeve (not shown) or other device, preferably having sidewall openings that correspond with the sidewall openings 408 formed in the extension tube 400, can also be placed over the extension tube 400, and optionally over the receiving member 108 as well, to prevent disengagement of the extension tube 400 from the receiving member 108 during use. Exemplary techniques for mating instruments such as the extension tube 400 to a polyaxial screw are disclosed in U.S. Pat. No. 7,666,188, the contents of which are incorporated by reference in their entirety. A person skilled in the art will appreciate that a variety of other techniques can be used to removably mate the extension tube 400 to a polyaxial screw.

As described above, polyaxial screws like those illustrated in FIGS. 1-3 can provide a number of advantages to surgeons, but are not without drawbacks. For example, the polyaxial movement of the receiving member 108 relative to the bone anchor 102 can aid in capturing a rod or other spinal fixation element after implantation in a patient's vertebra. This same movement, however, can limit a surgeon's control when applying corrective forces to the vertebra via the polyaxial screw in other portions of the procedure. The two-part set screws described above that can independently lock the polyaxial movement of the screw 100 and the position of the rod 206 can allow a surgeon to lock the screw in a monoaxial configuration, but surgeons often cannot tell if the screw is in a desired orientation when doing so. For example, surgeons often wish to lock the screw 100 in a monoaxial configuration when its receiving member 108 and bone anchor 102 are in a coaxial orientation (i.e., the longitudinal axis 124 of the bone anchor 102 is coaxial with the longitudinal axis 118 of the receiving member 108) to reduce the moment forces experienced by the screw when corrective forces are applied to the vertebra through the screw. It can be difficult to determine this orientation due to the fact that the bone anchor 102 is implanted in the vertebra and a rod or other spinal fixation element is seated within the receiving member 108. This problem can be exacerbated by the use of favored angle screws, as the receiving members of these screws have a non-symmetric range of motion and can move to a near-horizontal orientation in the favored direction. Surgeons can attempt to position a polyaxial screw in a coaxial orientation using a series of X-ray images to visualize the bone anchor 102 within the vertebra, but this is often time consuming, expensive, and it can expose the patient to additional radiation.

Instead, surgeons often compromise by utilizing different types of screws in different portions of a spinal fixation construct. For example, in spinal deformity correction procedures, a primary goal can be to align a patient's shoulders and pelvis (i.e., the top and bottom portions of the construct). Because there is a need to precisely determine the orientation of vertebrae in these locations, monoaxial screws are often used at the top and bottom of a pedicle screw construct. The monoaxial screws allow the surgeon to locate the screw in the vertebral body and use the exposed receiving member to indicate vertebral body orientation with a high level of precision. Monoaxial screws, however, do not conform to a rod and therefore make approximating and capturing the rod or other fixation element in the pedicle screw construct more difficult. In addition, using multiple types of screws in a procedure adds to the complexity and cost of the procedure.

Figure 6:
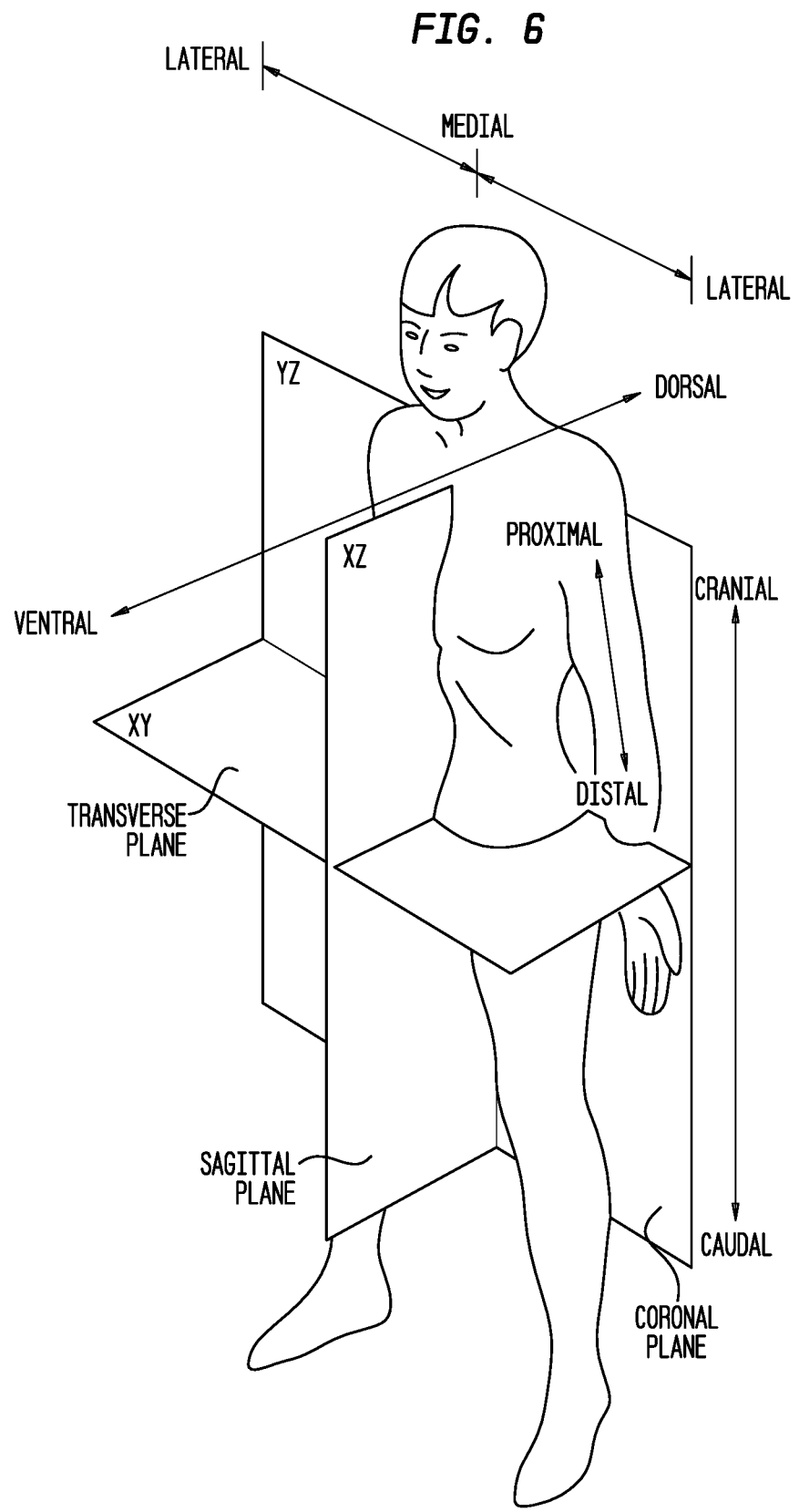
FIG. 6 is an illustration of the various anatomical planes and directions of the body.
Figure 7:
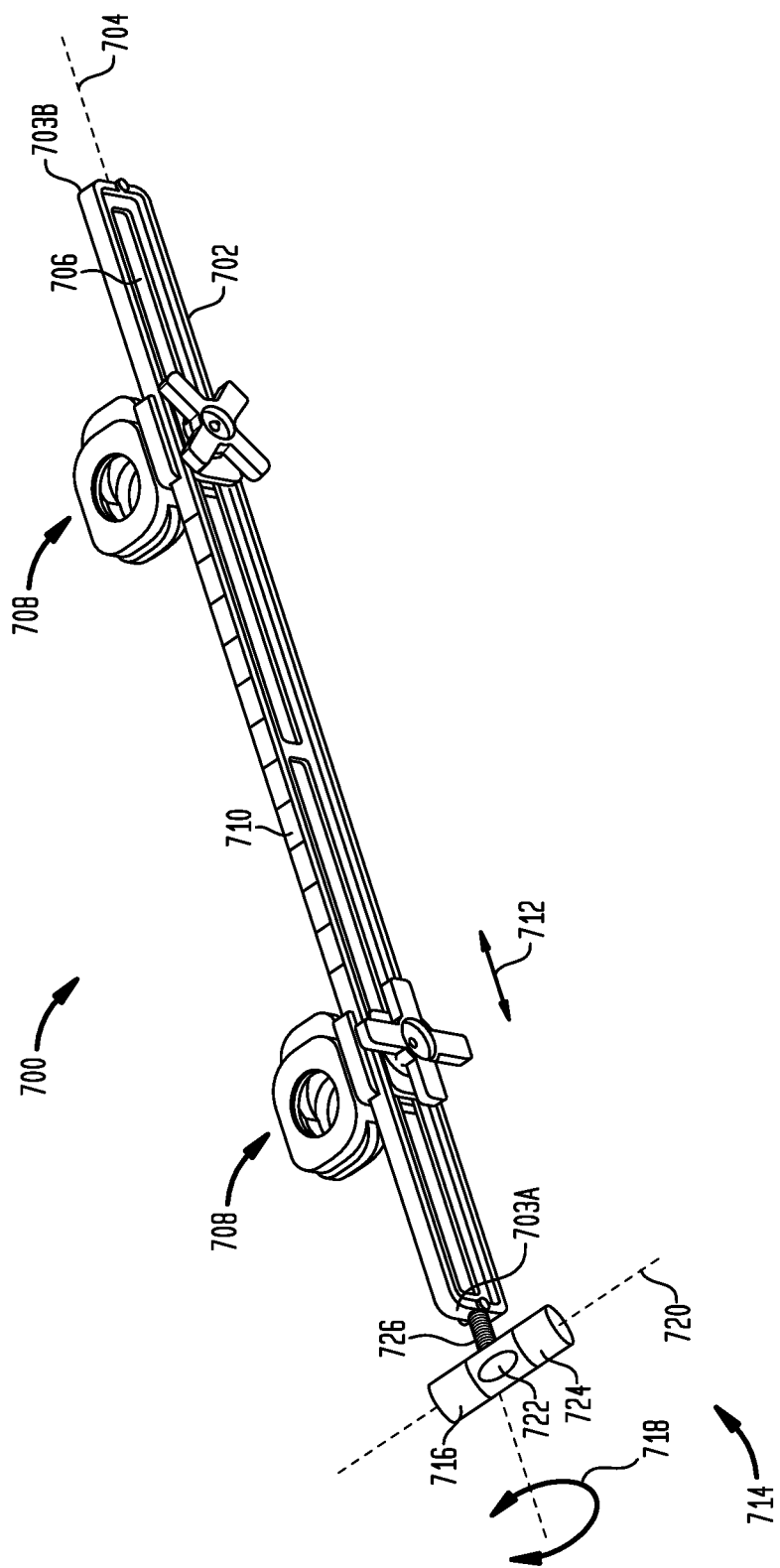
FIG. 7 is a perspective view of one embodiment of a polyaxial screw alignment instrument.
Figure 8:
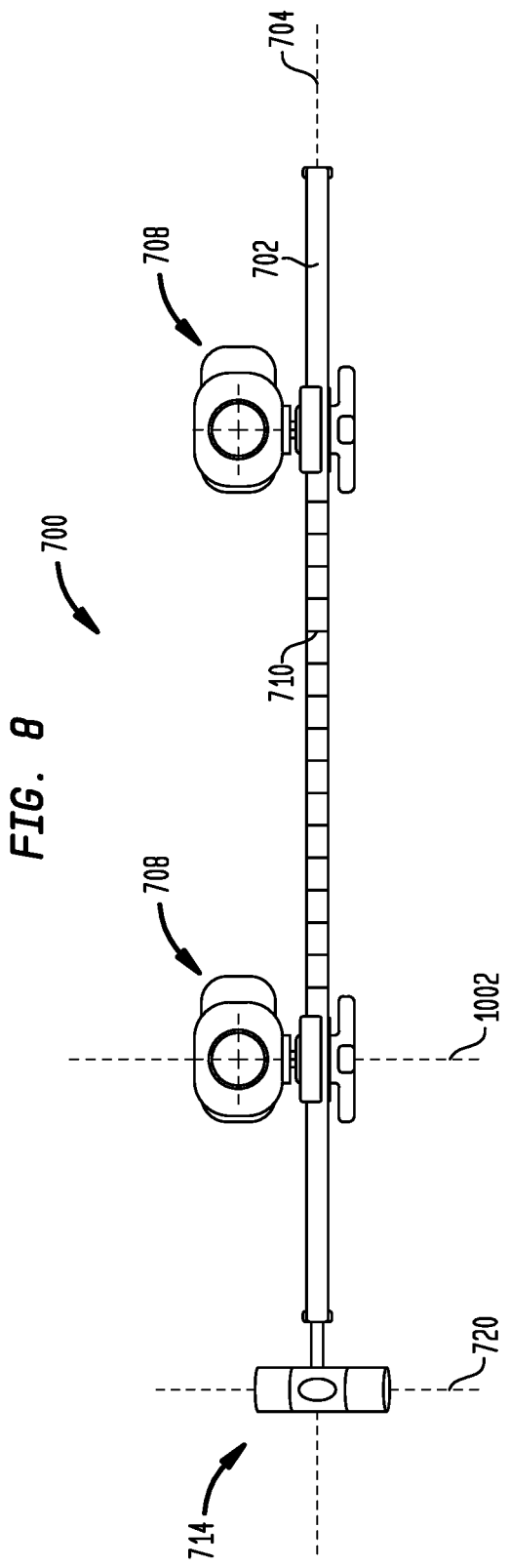
FIG. 8 is a top view of the polyaxial screw alignment instrument of FIG. 7.
Figure 9:
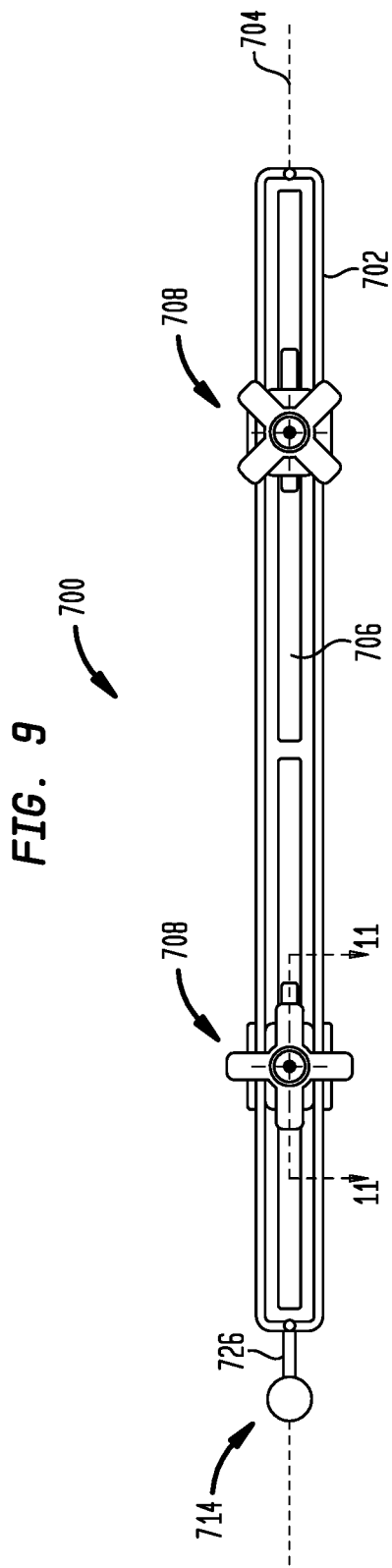
FIG. 9 is a rear view of the polyaxial screw alignment instrument of FIG. 7.

The methods and devices described herein can address these shortcomings by allowing surgeons to efficiently and effectively align the components of one or more polyaxial screws in a coaxial orientation. This, in turn, can permit surgeons to utilize a single polyaxial screw type throughout a spinal fixation construct. In general, the methods described herein include capturing the position and angular orientation of one or more polyaxial bone screws in a first plane, and then determining the angular orientation of the screws in a second plane transverse to the first plane. With reference to FIG. 6, for example, a method of aligning a plurality of polyaxial screws can include capturing the distance between and angular orientation of the plurality of polyaxial screws in the transverse plane of the body (i.e., in the medial/lateral directions). The plurality of polyaxial screws can be, for example, two polyaxial screws implanted bilaterally in a vertebra of a patient. The method can further include capturing the angular orientation of the screws in the sagittal plane of the body as well (i.e., in the cranial/caudal directions). Capturing the position and orientation of the screws in these two planes can allow a surgeon to return the screws to the same orientation at a later time and be assured that the receiving members and threaded shanks of the screws are again coaxially aligned.

FIGS. 7-11 illustrate one embodiment of a polyaxial screw alignment instrument 700 that can be used to capture the position and orientation of a plurality of polyaxial screws. The instrument 700 can include an elongate frame 702 having proximal and distal ends 703A, 703B, and a longitudinal axis 704 extending therethrough. The elongate frame can have a variety of shapes and sizes but, in some embodiments, can have a rectangular shape in which a length is larger than a width or depth of the frame. In certain embodiments, the length of the frame can be about 275 mm, with a width of about 15 mm and a depth of about 7 mm. The elongate frame 702 can in some embodiments include recessed areas formed on either side of the frame along a length thereof, thereby giving the frame a cross-sectional shape similar to an I-beam. Furthermore, the frame can include one or more through-channels 706 extending along a portion of the elongate frame to receive a plurality of connection caps 708 slidably disposed on the frame. Further, the elongate frame can include distance markings 710 that can be used to measure the distance between the plurality of connection caps 708, or between each of the plurality of connection caps 708 and a fixed point of reference on the elongate frame (e.g., the proximal end 703A of the elongate frame 702). The distance markings 710 can be imprinted on the elongate frame using any suitable manner known in the art, including, for example, ink printing, laser engraving, etching, grinding, etc.

As mentioned above, each of the plurality of connection caps 708 can be slidably disposed along the elongate frame 702 such that they can be translated along at least a portion of the frame between the proximal and distal ends 703A, 703B, as shown by arrows 712. As is best shown in the exploded view of FIG. 10, each connection cap 708 can include several components that allow the connection cap to translate along the length of the elongate frame 702, rotate relative to the frame about an axis 1002 extending through the frame, and selectively lock relative to the frame such that neither rotation nor translation is permitted.

Figure 10:
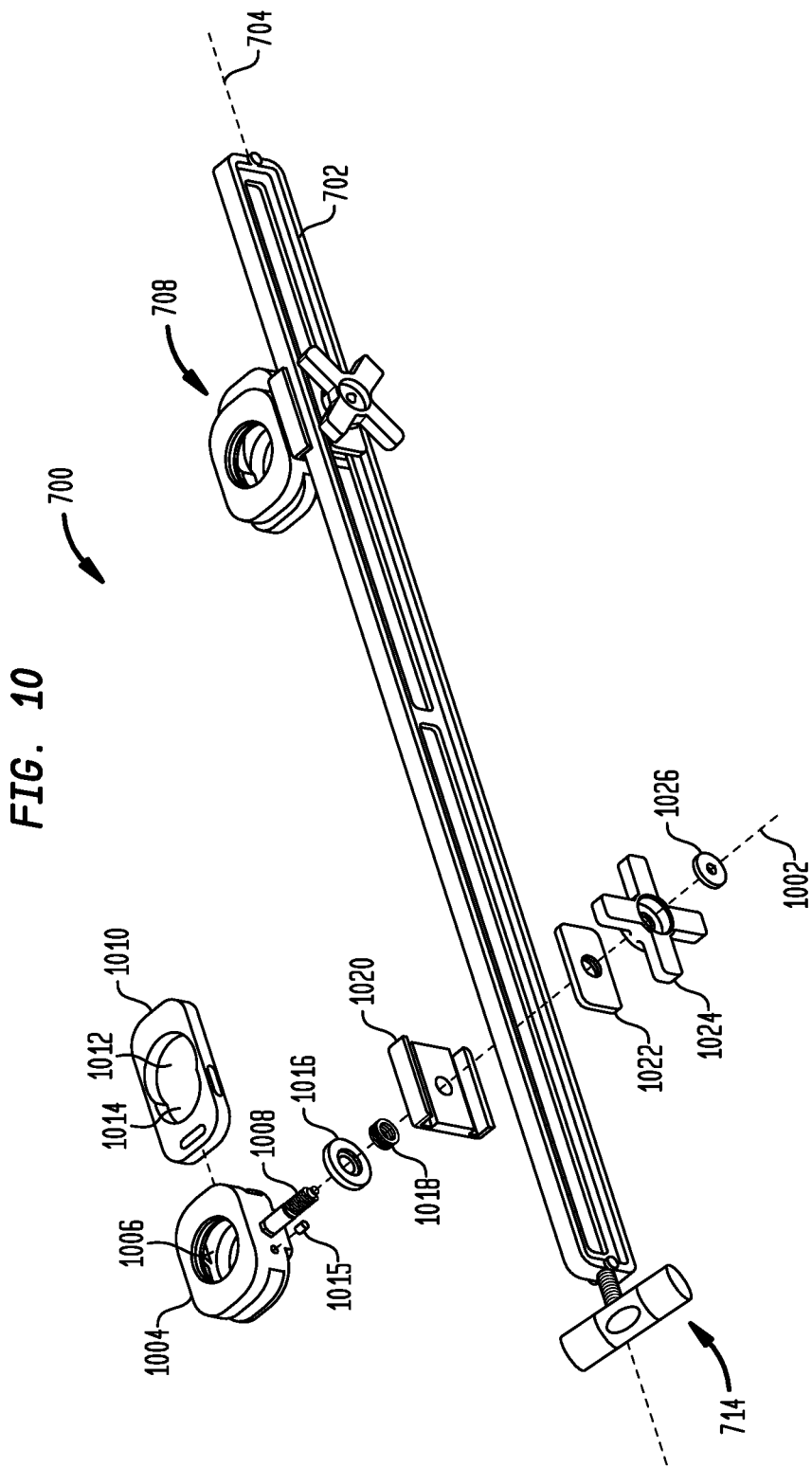
FIG. 10 is an exploded view of the polyaxial screw alignment instrument of FIG. 7.

In the illustrated embodiment, and with particular reference to FIG. 10, each connection cap 708 can include a connection cap body 1004 having an inner lumen 1006 configured to receive the proximal end of a polyaxial screw extension tube (e.g., polyaxial screw extension tube 400 discussed above), and a cantilever shaft 1008 extending from a sidewall thereof that is configured to extend through the channel 706 formed in the elongate frame 702. The connection cap body can have a variety of shapes and sizes but, in some embodiments, can be sized such that the inner lumen 1006 extending therethrough is large enough to receive the outer diameter of an extension tube.

Figure 11:
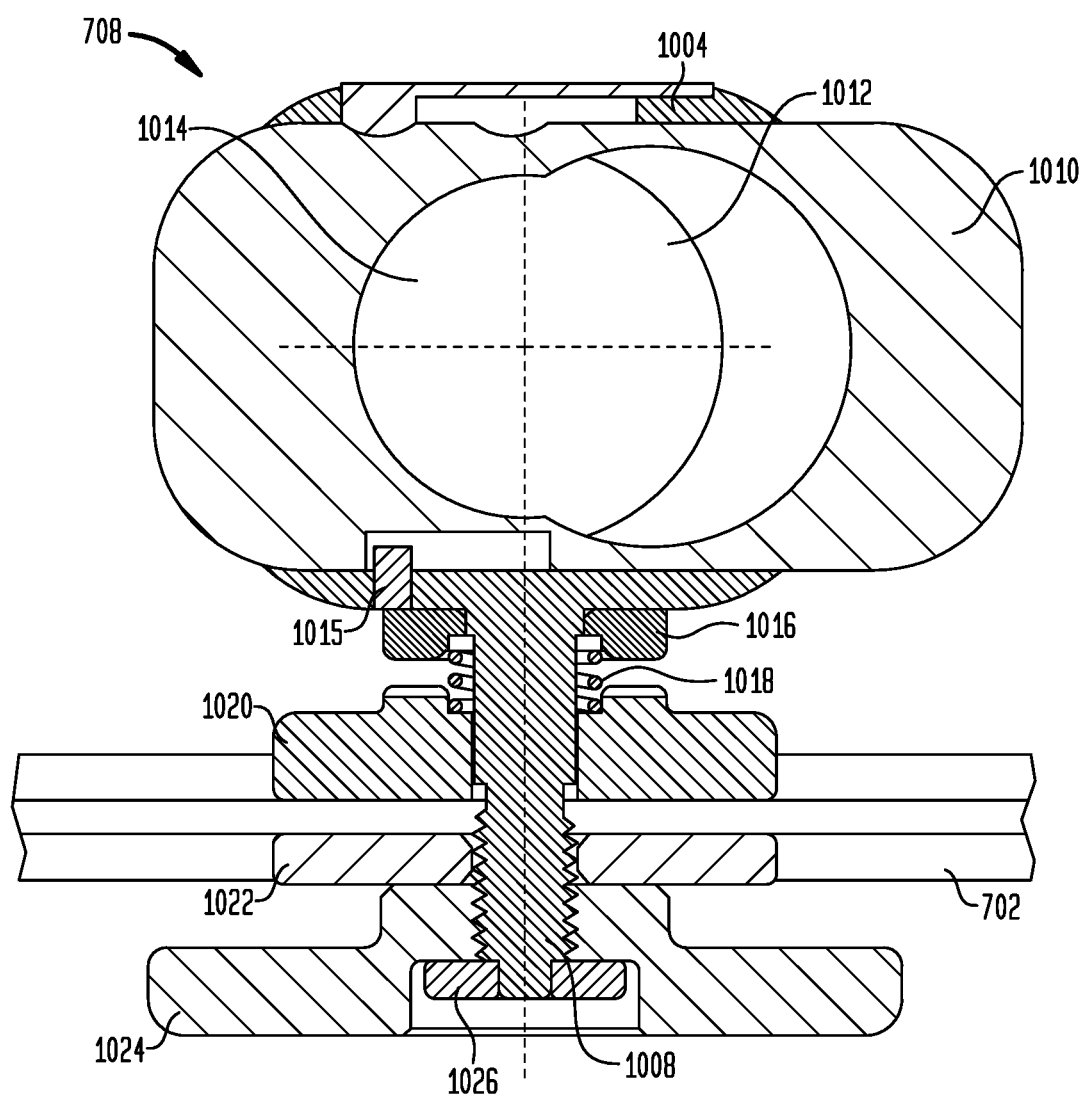
FIG. 11 is a cross-sectional view of a portion of the polyaxial screw alignment instrument of FIG. 7.

Slidably disposed within the connection cap body 1004 can be an extension tube locking member 1010 that is configured to selectively lock the connection cap body to the proximal end of a polyaxial screw extension tube. The tube locking member 1010 can also include an inner lumen formed therein, and the inner lumen can be divided into an enlarged portion 1012 and a constricted portion 1014. The enlarged portion 1012 can have a diameter at least as large as the diameter of the inner lumen 1006 of the connection cap body 1004 so that the proximal end of a polyaxial screw extension tube can be received therethrough. The constricted portion 1014, however, can have a reduced diameter configured to interface with a notch or other complementary feature formed on an outer surface of a polyaxial screw extension tube. FIG. 11 illustrates the connection cap 708 in cross section and shows the interaction between the connection cap body 1004 and the tube locking member 1010. In particular, the tube locking member 1010 can be slidably disposed within the connection cap body 1004 and its movement can be constrained by an alignment pin 1015. In this configuration, the tube locking member 1010 can move between a first position in which the enlarged portion 1012 of the inner lumen of the tube locking member 1010 is aligned with the inner lumen 1006 of the connection cap body 1004, and a second position in which the constricted portion 1014 of the inner lumen of the tube locking member 1010 is aligned with the inner lumen 1006 of the connection cab body 1004 (as shown in FIG. 11).

Figure 12A:
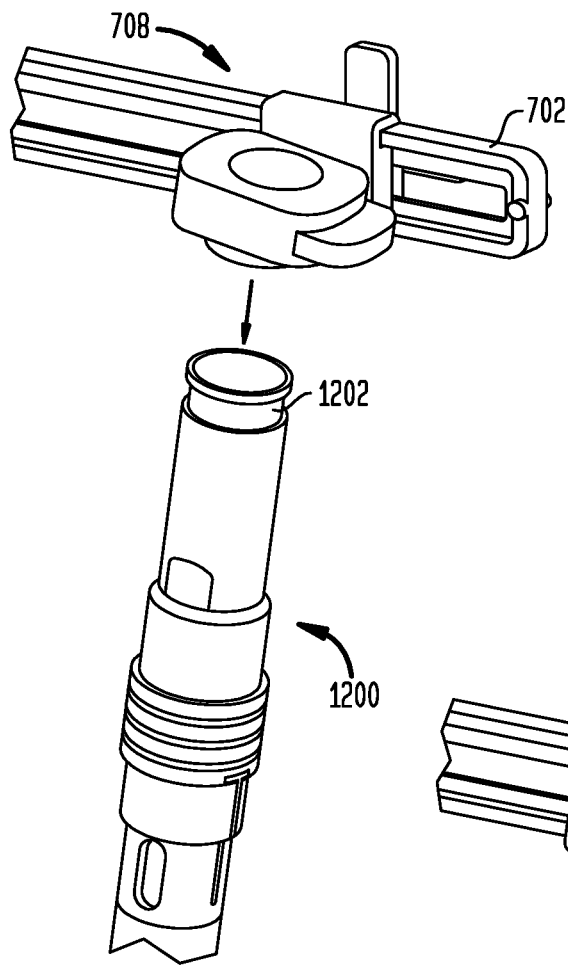
FIG. 12A illustrates the operation of one embodiment of a connection cap.
Figure 12B:
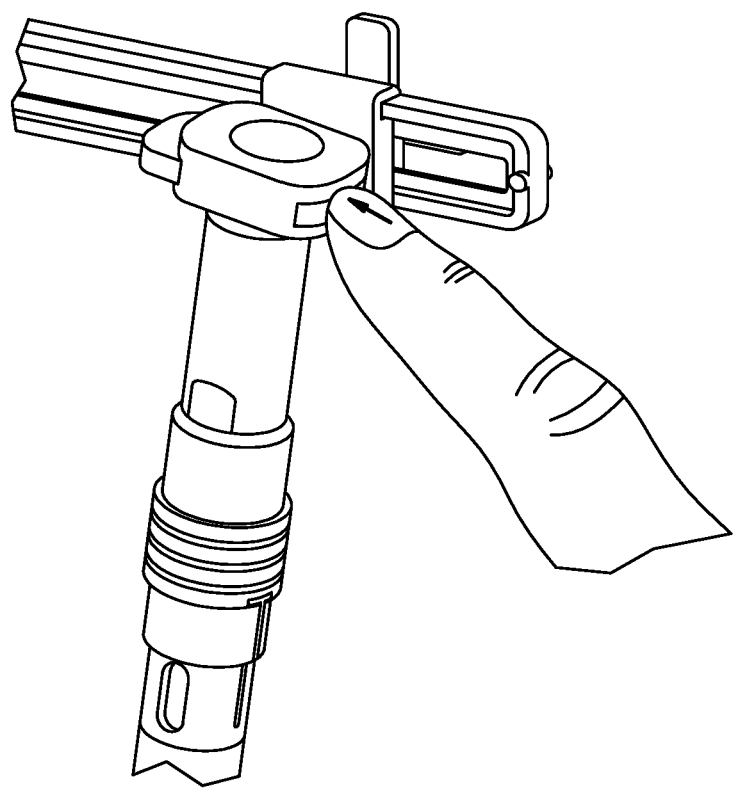
FIG. 12B illustrates another view of the operation of the connection cap of FIG. 12A.

FIGS. 12A-12B illustrate the resulting operating of the connection cap 708. To begin, the tube locking member 1010 can be moved to the first position such that the full diameter of the inner lumen 1006 of the connection cap body 1004 is open. As shown in FIG. 12A, the connection cap 708 can then be lowered on top of a proximal end of a polyaxial screw extension tube 1200. The extension tube 1200 can include an annular groove 1202 formed at a proximal end thereof that has an outer diameter substantially equal to the diameter of the constricted portion 1014 of the tube locking member 1010. To releasably lock the connection cap 708 to the extension tube 1200, a user can slide the tube locking member 1010 from the first position (as shown in FIG. 12A) to the second position (as shown in FIG. 12B), which can bring the constricted portion 1014 of the tube locking member 1010 into contact with the annular groove 1202 formed in the extension tube 1200.

Referring back to FIG. 10, a retaining washer 1016 can be placed over the shaft 1008 such that it abuts against the connection cap body 1004 and holds the alignment pin 1015 within a through-hole formed in the connection cap body. A coil spring 1018 can be placed over the shaft 1008 as well to prevent the various components of the connection cap 708 from becoming loose when the connection cap 708 is not locked to the elongate frame 702.

The connection cap 708 can be coupled to the elongate frame 702 using first and second sliding members 1020, 1022 disposed on opposite sides of the elongate frame 702. The first sliding member 1020 can have a shape that complements the profile of an outer surface of the elongate frame 702. For example, and as shown in FIGS. 10-11, the first sliding member 1020 can have a rectangular shape and include parallel recessed channels extending along a length thereof such that the first sliding member 1020 can fit over one three sides of the elongate frame 702. The second sliding member 1022 can have a rectangular shape and can be sized such that it fits within the recessed area formed on one side of the elongate frame 702. Both the first and second sliding members 1020, 1022 can include through-holes formed therein that are configured to receive the shaft 1008 of the connection cap body 1004.

Selective locking of the connection cap 708 with respect to the elongate frame 702 can be accomplished using the thumbscrew 1024 that engages with threads formed on a portion of the shaft 1008 of the connection cap body 1004. By tightening the thumbscrew 1024, the first and second sliding members 1020, 1022 can be compressed against the elongate frame 702 such that sliding motion with respect to the elongate frame is prohibited. Furthermore, by tightening the thumbscrew 1024, the connection cap body 1004 can be securely pressed against the first sliding member 1020, thereby preventing the connection cap body from rotating with respect to axis 1002. In addition, a retaining washer 1026 can be rigidly coupled to the distal end of the shaft 1008 such that the thumbscrew 1024 cannot be loosened to a point where it disengages from the shaft 1008. Accordingly, the thumbscrew can effect the selective locking of the connection cap 708 with respect to the elongate frame such that the position and angular orientation of the connection cap 708 (and any polyaxial screw extension tube coupled thereto) relative to the elongate frame can be captured and/or maintained.

While FIGS. 10-13C illustrate the use of a connection cap 708 to engage a proximal portion of extension tube 1200 and thereby connect the extension tube to the elongate frame, a person of skill in the art will appreciate that alternative connection schemes can be used. For example, a variety of clamp-like elements can be used to engage either a proximal portion of the extension tube or a portion of the extension tube intermediate the proximal and distal ends of the extension tube. An example of such a clamp-like element is described below and illustrated in FIG. 21.

One of skill in the art will appreciate that the embodiments described above provide examples of a few of many of possible mechanisms for slidably disposing a connection cap to an elongate frame such that the connection cap can be selectively locked in position and orientation relative to the frame. The above-described embodiments, or any other embodiments known in the art, can be constructed in a variety of sizes depending on intended use, size and number of polyaxial screw extension tubes, patient anatomy, etc. Further, the components can be constructed from any suitable biocompatible material, such as stainless steel, or a polymer, and can be constructed using any conventional method of manufacturing medical devices.

For example, FIGS. 13A-13C illustrate variations on the thumbscrew 1024 that can be included in the assembly of a connection cap 708. FIG. 13A illustrates a thumbscrew 1300 having short arms to reduce the overall size of the thumbscrew 1024. To aid in leveraging the thumbscrew 1024 when selectively locking a connection cap's position and/or orientation, the thumbscrew can include one or more recesses (not shown) that can receive a driving tool 1302. FIG. 13B illustrates an alternative embodiment of a thumbscrew 1304 that is similar in shape to thumbscrew 1024. The thumbscrew 1304 can have longer arms than the thumbscrew 1300 to provide greater leverage. In such an embodiment, a tool 1306 can be configured to simply slide over one of the arms to extend its length and increase a user's mechanical advantage when tightening the thumbscrew. FIG. 13C illustrates still another alternative embodiment in which a cylindrical thumbscrew 1308 is provided in place of a thumbscrew having separate arms. One of skill in the art will appreciate that there are a variety of other possible configurations for the thumbscrew or other components of the connection cap 708 that can be used without departing from the teachings of the present invention. For example, although not illustrated, the thumbscrew can be oriented so as to be in a plane that is substantially transverse or otherwise angularly oriented with respect to a longitudinal axis of the extension tube.

Referring back to FIGS. 7-10, the polyaxial screw alignment instrument 700 can also include a transverse angle indicator 714 that can be coupled to the elongate frame 702. The transverse angle indicator 714 can indicate an angular orientation of the elongate frame 702 in a plane that is transverse to the longitudinal axis 704 of the elongate frame. In the illustrated embodiment, the transverse angle indicator 714 can include a bubble level 716 rotatably coupled to the elongate frame 702 at the proximal end 703A thereof. The bubble level can be configured to rotate (as shown by arrows 718) in a plane that is transverse to the longitudinal axis 704 of the elongate frame 702. In some embodiments, the plane can be perpendicular to the longitudinal axis 704. In the illustrated embodiment, for example, the plane of rotation extends along the longitudinal axis 720 of the bubble level 716 that is perpendicular to the longitudinal axis 704 of the elongate frame 702. As mentioned above, however, in other embodiments the transverse plane need not be perpendicular, but can be angularly offset from the longitudinal axis 704 by some other amount.

Figure 19:
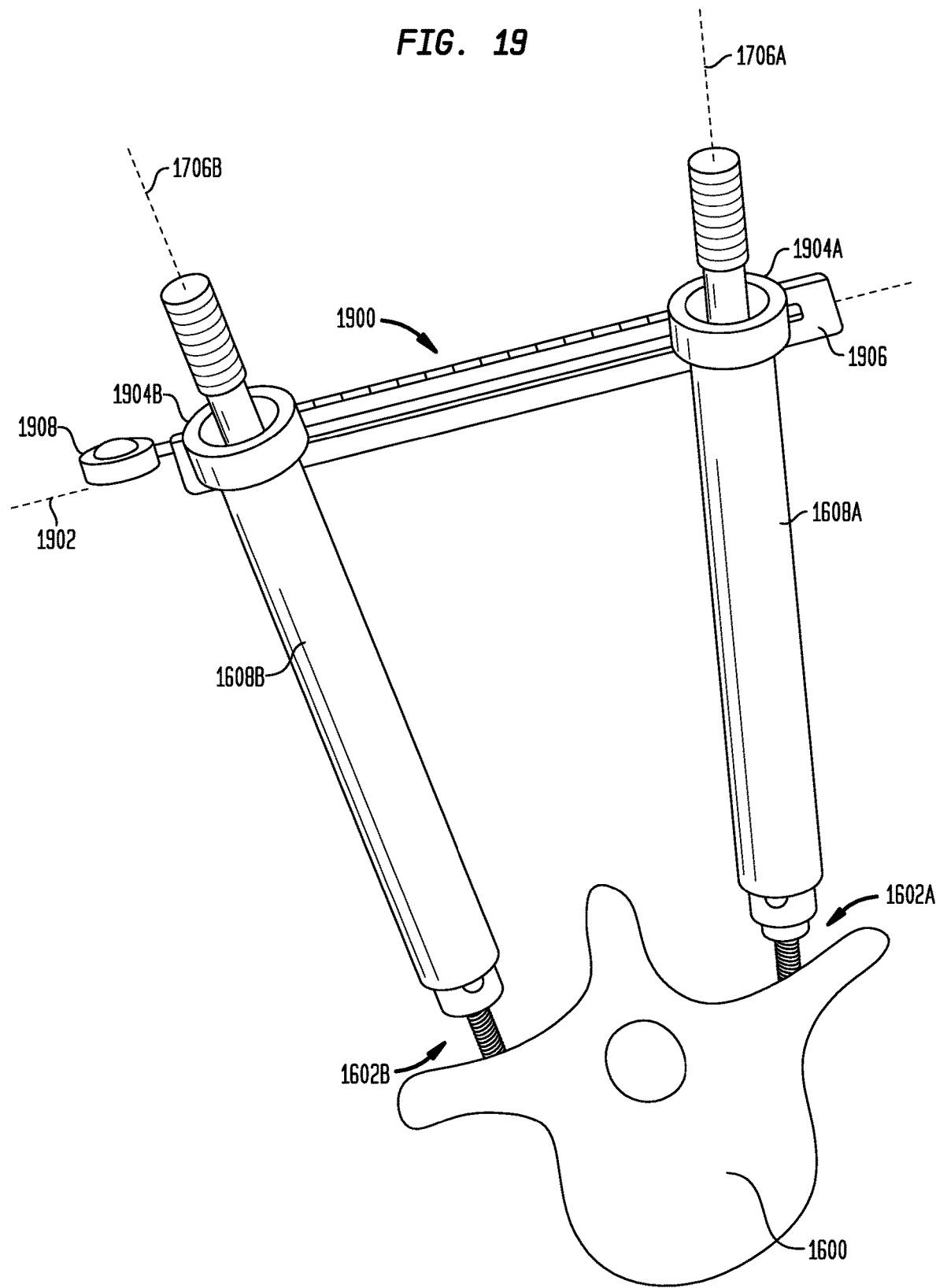
FIG. 19 illustrates the polyaxial screws, extension tubes, and alignment shafts of FIG. 17 having a polyaxial screw alignment instrument coupled thereto.

The bubble level 716 illustrated in FIGS. 7-10 can have a variety of shapes and sizes. In the illustrated embodiment, the bubble level 716 has a generally cylindrical shape that defines the longitudinal axis 720. The bubble level 716 can be a sealed transparent member partially filled with a liquid such that an air bubble 722 remains within the sealed member. The bubble level 716 can include any number of markings 724 that can aid a user in determining when the bubble level 716 is in a level orientation. In other embodiments, alternative bubble level designs can be employed, including, for example, hemispherical bubble levels (as shown in FIG. 19) and other known designs.

The bubble level 716 can be coupled to the elongate frame 702 by a rotating member 726 such that the bubble level can be rotated within a plane transverse to the longitudinal axis 704 of the elongate frame. The rotating member 726 can have a variety of lengths, shapes, and mechanical configurations. For example, in some embodiments the rotating member 726 can include a cantilever shaft extending from the elongate frame 702 and a cylindrical sleeve extending from an outer surface of the bubble level 716. The cylindrical sleeve can include a bore formed therein sized to receive the shaft extending from the elongate frame 702, and the outer surface of the shaft and inner surface of the sleeve bore can include threads to rotatably engage one another. Furthermore, in some embodiments, the rotating member 726 can include a set screw or other position-retention mechanism to allow the bubble level 716 to be locked in a particular orientation relative to the elongate frame 702.

To use the transverse angle indicator 714, a user can place the elongate frame and plurality of connection caps in a desired orientation (e.g., by coupling the plurality of connection caps to a plurality of polyaxial screw extension tubes, as described below) and then rotate the bubble level 716 until the air bubble 722 indicates that the bubble level is in a level orientation (e.g., the air bubble 722 is positioned at the center of the bubble level 716 between two markings 724). The user can then lock the bubble level 716 in this orientation (if a locking feature is present) for future reference. To return the frame to the same orientation with respect to the transverse plane, a user can simply rotate the elongate frame 702 in the transverse plane until the bubble level 716 again indicates that it is in a level orientation.

FIG. 14 illustrates an alternative embodiment of a polyaxial screw alignment instrument 1400 that includes a different transverse angle indicator 1402. The transverse angle indicator 1402 includes an angular scale 1404 that can be rotatably mounted to the elongate frame 1406 at a pivot point 1408. To use the transverse angle indicator 1402, a user can position instrument 1400 in a desired orientation and then rotate the angular scale 1404 until one of its edges aligns with a vertical or horizontal direction. The user can then correlate a marking formed on the elongate frame 1406, or an edge of the frame itself, with a degree marking on the angular scale 1404 to determine the angular orientation of the instrument 1406 in a plane transverse to a longitudinal axis 1410 of the elongate frame 1406.

Of course, the illustrated embodiment is just one example of an angular scale that can be utilized in the polyaxial screw alignment instrument 1400. For example, in other embodiments an angular scale similar to the scale 1404 can be rigidly mounted to the elongate frame 1406 and can include a small weight hanging from a string that can act as a vertical plumb. As the elongate frame is positioned, the hanging string can move across the angular scale and indicate the angular orientation of the instrument in a plane transverse to a longitudinal axis of the elongate frame. In another embodiment, a laser or similar light emitting element can be rotatably mounted to the frame and configured in such a way (e.g., by the use of one of more weighted elements) that the light emitted by the laser is always directed vertically by the effects of gravity. As in the embodiment described above, the light can be directed to an angular scale to indicate the angular orientation of the instrument in a plane transverse to a longitudinal axis of the elongate frame. Still further, the features of the various embodiments described herein can be combined with one another. For example, the angular scale 1402 can include a bubble level similar to the level 716 rigidly mounted thereto such that a user can more easily align the scale with a vertical or horizontal direction. In other embodiments, an angular scale can be added to the transverse angle indicator 714 such that a user can capture the angular orientation of the instrument 700 by recording the exact angular orientation rather than locking the bubble level 716 in an particular orientation.

Figure 15:
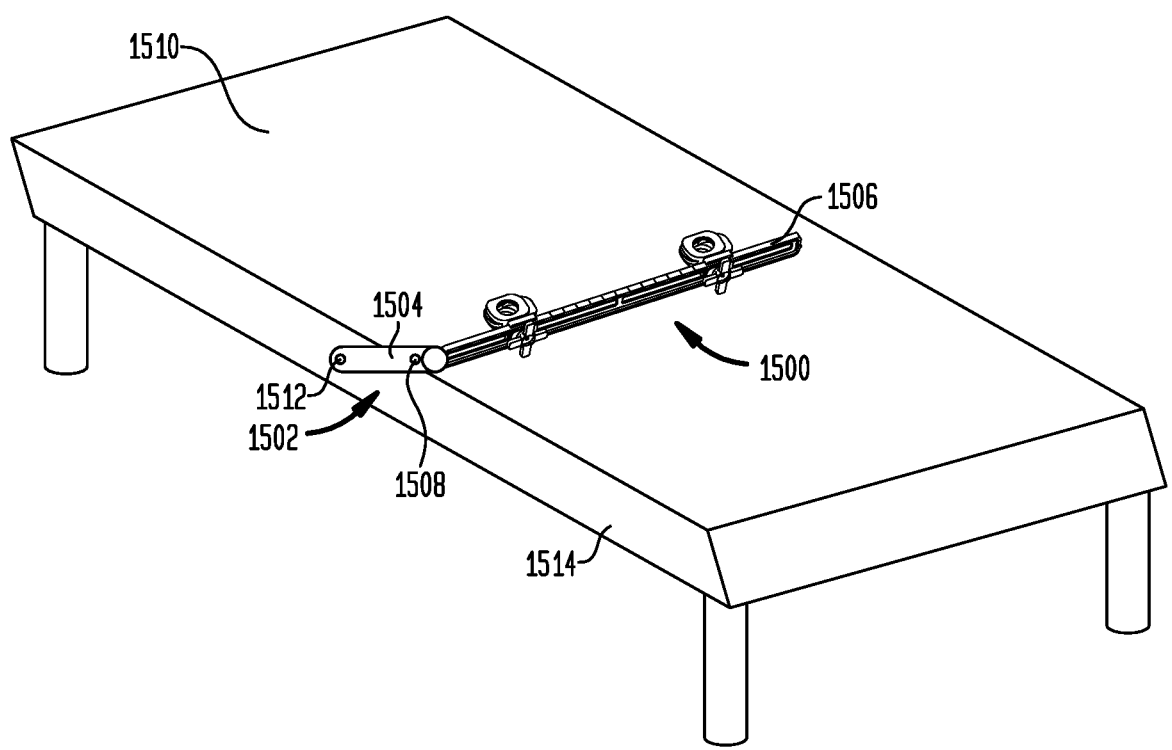
FIG. 15 is a perspective view of an alternative embodiment of a polyaxial screw alignment instrument.

FIG. 15 illustrates still another embodiment of a polyaxial screw alignment instrument 1500 that includes another embodiment of a transverse angle indicator 1502. In the illustrated embodiment, the transverse angle indicator 1502 can include a rigid arm 1504 rigidly coupled at one end to the elongate frame 1506 at point 1508, and rotatably coupled at the other end to an operating surface 1510 or other fixed object at pivot point 1512. The arm 1504 can be constrained to rotate about the pivot point 1512 through a single plane, e.g., the plane defined by the sidewall 1514 of the operating surface 1510. As a result, the position of the arm can indicate the angular orientation of the elongate frame 1506 with respect to the operating surface 1510. Because the position and orientation of the operating surface 1510 does not change throughout the procedure, it can serve as a reference frame for orienting the elongate frame 1506, just as the constant direction of gravity does in the previously-described embodiments.

The arm 1504 can include a number of previously-described features to aid a user in capturing and returning to a particular angular orientation at different times during a procedure. For example, the arm can include an angular scale coupled thereto (or disposed on the sidewall 1514 of the operating surface 1510) to allow a user to read off the exact angular orientation of the arm 1504, or the arm can include a set screw or other retaining feature to allow the arm to be locked in a given orientation as desired. Furthermore, the elongate frame 1506 can be removably coupled to the arm 1504 at point 1508, and the arm can be removably coupled to the operating surface 1510 at point 1512. This can allow the elongate frame 1506, or the elongate frame and arm 1504, to be removed when not in use and reattached when necessary. Still further, the arm 1504 can have a telescoping length to accommodate various operating heights, and can be configured to attach to the operating surface 1510 at various locations, e.g., various locations along the length of the operating surface sidewall 1514.

Figure 16:
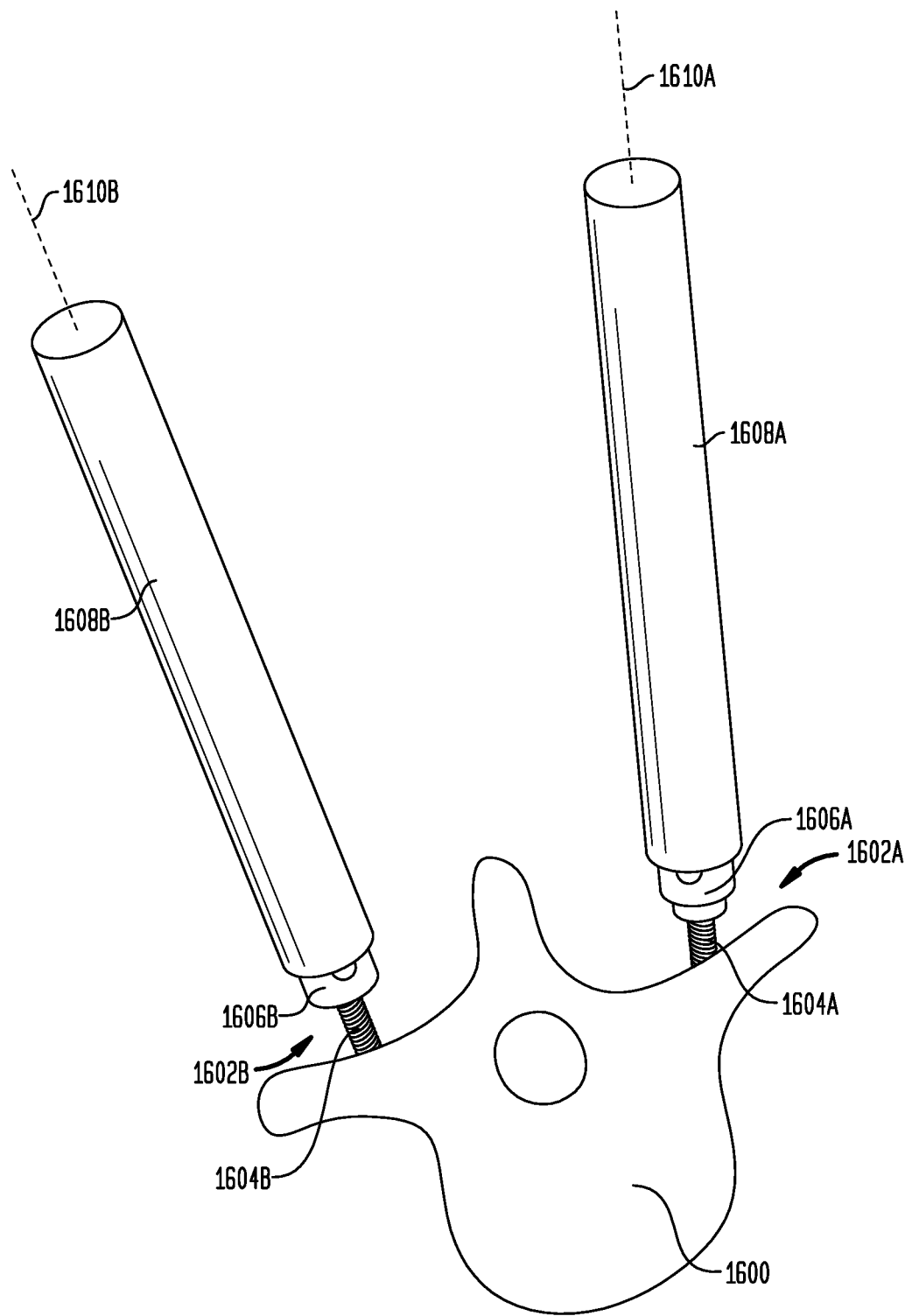
FIG. 16 illustrates a plurality of polyaxial screws having extension tubes coupled thereto implanted in a patient's vertebra.
Figure 17:
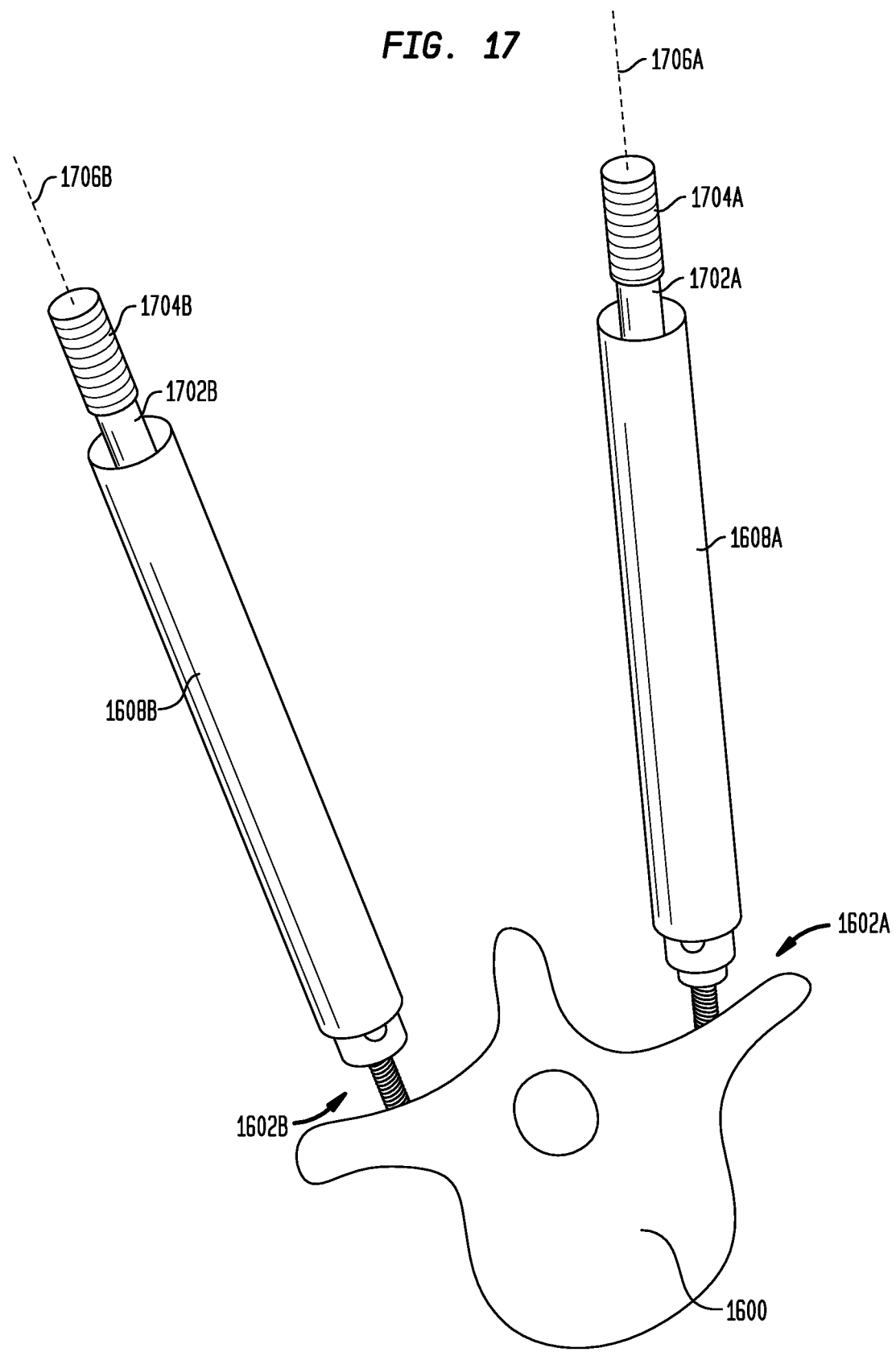
FIG. 17 illustrates the polyaxial screws and extension tubes of FIG. 16 having alignment shafts coupled thereto.

FIGS. 16-19 illustrate an exemplary method for use of a polyaxial screw alignment instrument as described herein. The method can include implanting in a vertebra one or more polyaxial bone screws having a receiving member that is polyaxially movable relative to a threaded shank implanted within the vertebra. In FIG. 16, for example, two polyaxial screws 1602A, 1602B are shown implanted in a bilateral configuration in vertebra 1600. Each polyaxial screw 1602A, 1602B can include a threaded shank 1604A, 1604B and a receiving member 1606A, 1606B coupled to the threaded shank 1604A, 1604B. The method can also include coupling a polyaxial screw extension tube, such as the extension tubes 1608A, 1608B, to each of the receiving members 1606A, 1606B.

In the configuration shown in FIG. 16, the extension tubes 1608A, 1608B are coupled to the receiving members 1606A, 1606B such that a longitudinal axis 1610A, 1610B of each extension tube is coaxial with a longitudinal axis of the receiving member it is coupled to. Furthermore, each extension tube and receiving member pair can move polyaxially with respect to the threaded shank 1604A, 1604B that it is coupled to.

Prior to capturing a rod or other spinal fixation element within the receiving members 1606A, 1606B of the polyaxial screws 1602A, 1602B, an alignment shaft, such as the alignment shafts 1702A, 1702B, can be inserted into each of the extension tubes 1608A, 1608B. Each of the alignment shafts 1702A, 1702B can be a rigid, elongate shaft having a handle, such as the handles 1704A, 1704B, at a proximal end thereof and an engagement portion at a distal end thereof that can be configured to interface with both the receiving member and the threaded shank of a polyaxial screw in a manner that locks the two components in a coaxial orientation. Each alignment shaft can have a longitudinal axis 1706A, 1706B extending between the proximal and distal ends thereof.

Figure 18:
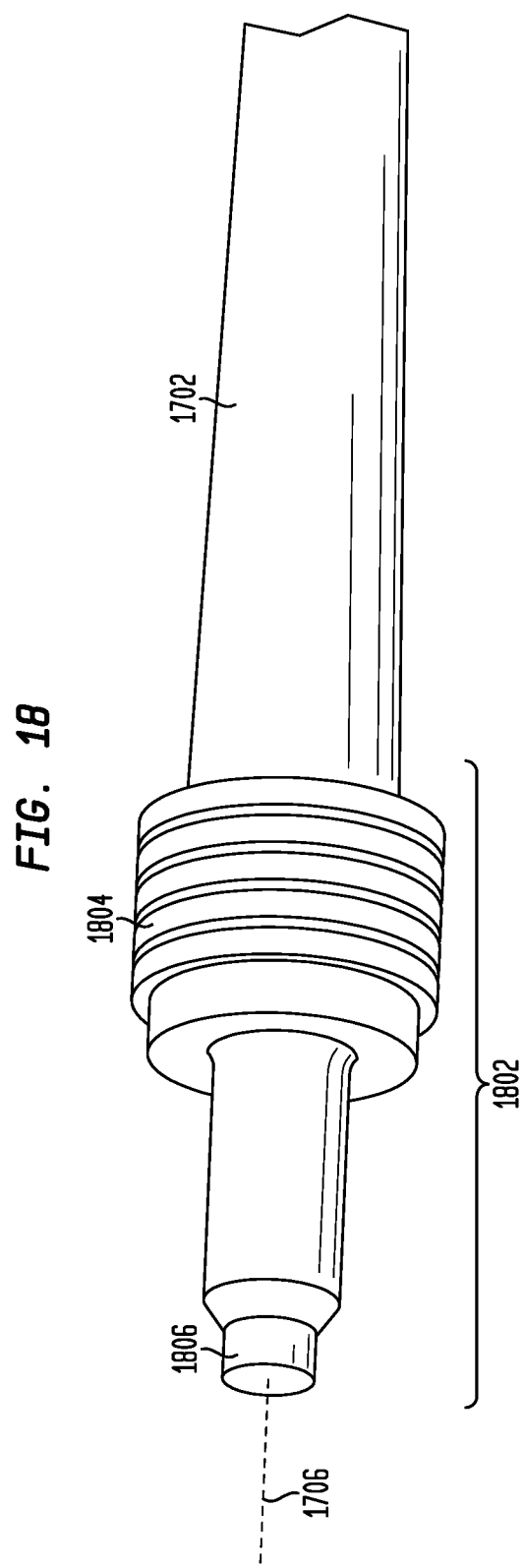
FIG. 18 is a perspective view of one embodiment of an alignment shaft.

FIG. 18 illustrates one embodiment of a distal end of an alignment shaft 1702 that includes an engagement portion 1802. The engagement portion 1802 can include separate components configured to interface with each of the receiving member and the threaded shank of a polyaxial screw. In the illustrated embodiment, for example, the engagement portion 1802 can include external threads 1804 configured to engage with the internal threads formed on the receiving member, e.g., the threads formed on the legs 124A, 124B of the receiving member 108 shown in FIGS. 1-2. The engagement portion 1802 can also include a protrusion 1806 formed on a distal end of the alignment shaft 1702 and configured to interface with a recess or driving feature provided on the threaded shank of a polyaxial screw, e.g., the recess 202 formed in the head 104 of the bone anchor 102 shown in FIG. 2. In this embodiment engagement between the alignment shaft 1702 and the threaded shank of a polyaxial screw, such as through protrusion 1806 and the recess of the threaded shank of a polyaxial screw) can be effective to coaxially align the threaded shank and the alignment shaft.

Figure 18A:
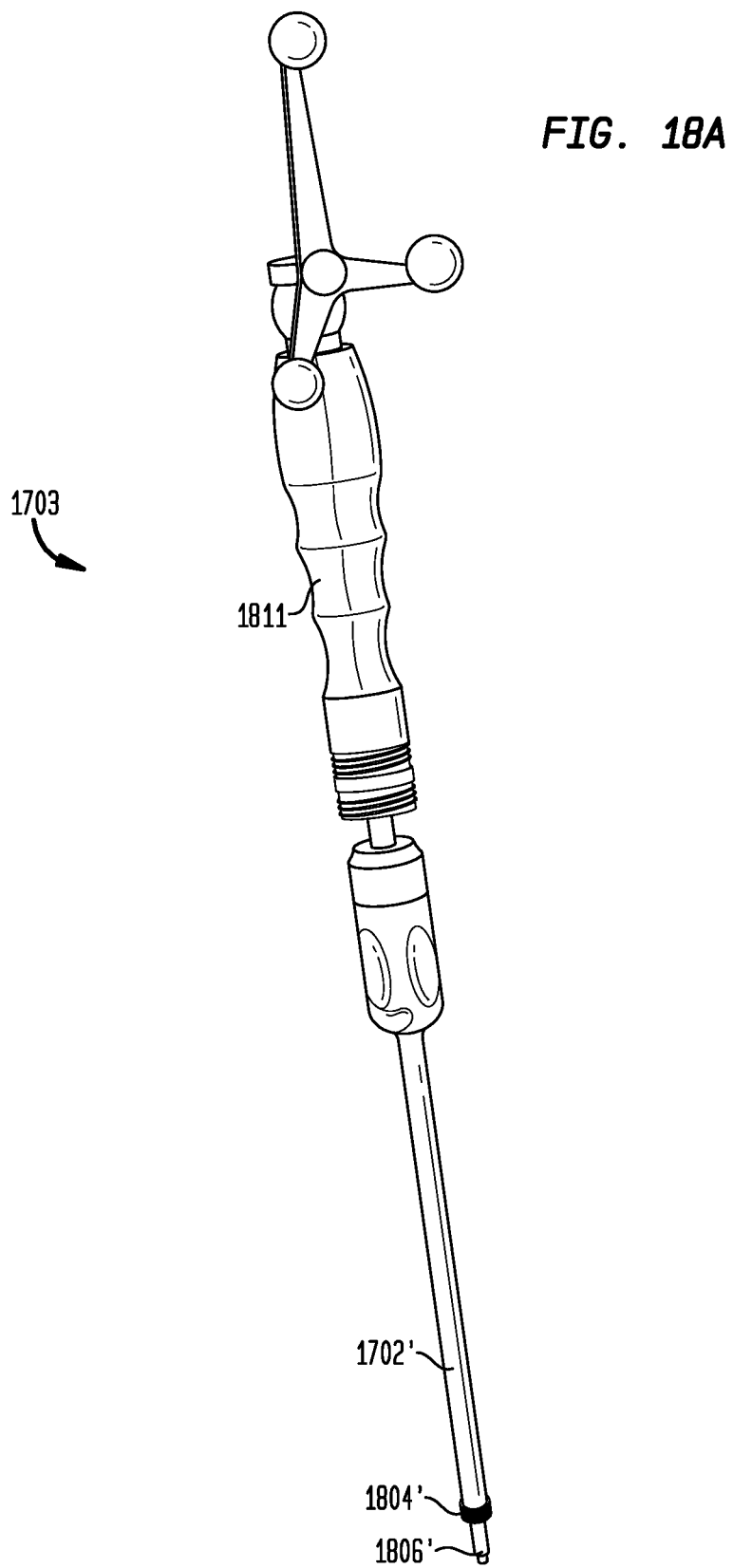
FIG. 18A is a perspective view of one embodiment of an alignment shaft assembly.

In another embodiment, shown in FIG. 18A, an alternative alignment shaft assembly 1703 is shown. Rather than a one-piece member such as alignment shaft 1702 of FIG. 18, alignment shaft assembly 1703 is a two-piece member, which is effective to coaxially align the threaded shank and the alignment shaft as well as to facilitate driving of the threaded shank. Alignment shaft assembly 1703 includes a shaft 1702' and external threads 1804' similar to the shaft 1702 and protrusion with external threads 1804 described above for the one-piece embodiment of FIG. 18. However, shaft 1702' includes a lumen (not shown) extending longitudinally therethrough and it terminates with the external threads 1804'. The two-piece embodiment further includes, as a second component, an elongate drive member that extends from a proximal handle 1811 to the drive member 1806', shown in FIG. 18A as protruding from the distal end of the alignment shaft 1702'. FIG. 18A shows the drive member 1806' disposed within the lumen of the shaft 1702', however it is understood that the drive member can be removably and replaceably disposed within the lumen of shaft 1702'. In this embodiment, the elongate drive member, as a separate member, may be passed through the lumen of the shaft 1702' so as to extend distally beyond the external threads 1804' at the distal end of shaft 1702'. As a separate element, the drive member can be manipulated independently of the shaft 1702. For example, when the drive member 1806' is engaged with the recess of the threaded shank, the drive member 1806' can be manipulated such as by rotating handle 1811 to advance the threaded shank of the bone anchor.

By driving each of the alignment shafts 1702A, 1702B into the polyaxial screws 1602A, 1602B such that the engagement portion of each alignment shaft interfaces with both the threaded shanks 1604A, 1604B and the receiving members 1606A, 1606B of the screw, the alignment shafts can ensure that the longitudinal axes of the threaded shanks 1604A, 1604B, receiving members 1606A, 1606B, and extension tubes 1608A, 1608B are each coaxial with the longitudinal axes 1706A, 1706B of the alignment shafts. This is the configuration shown in FIG. 17.

An alignment shaft similar to shafts 1702A, 1702B can provide an easy way to ensure the coaxial alignment of a screw extension tube, receiving member, and threaded shank, but the alignment shaft cannot be used after a spinal fixation element is passed through the receiving member because the spinal fixation element blocks access to the recess or other driving feature formed in the head of the threaded shank. Accordingly, the method can include capturing the position and/or angular orientation of one or more polyaxial screws and extension tubes when alignment shafts are present using an instrument that can be re-applied after spinal fixation shaft capture, or some other procedure, prevents the use of the alignment shafts.

For example, and as shown in FIG. 19, the method can include coupling a polyaxial screw alignment instrument 1900 to the proximal ends of each of the polyaxial screw extension tubes 1608A, 1608B and selectively locking the instrument 1900 to indicate a distance between and an angular orientation of each of the extension tubes relative to a longitudinal axis 1902 of the instrument 1900. This can be accomplished, for example, using a connection cap of the instrument 1900, such as the connection caps 1904A, 1904B, to couple the instrument to the proximal ends of one or more extension tubes, such as extension tubes 1608A, 1608B. The measurements captured in this manner lie only in a single plane, however. For example, in the embodiment shown in FIG. 19, the measurements are captured in the transverse plane of the body, which extends along the longitudinal axis 1902 of the elongate frame 1906.

In addition to the mechanical devices described above that indicate a distance between and an angular orientation of each of the extension tubes relative to a longitudinal axis 1902 of the instrument 1900, a person of skill in the art will appreciate that a variety of electrical and/or optical devices can be utilized as well. For example, sensors (not shown) can be placed on the alignment shafts and/or the caps 1904A, 1904B (or other clamping devices) that secure the extension tube to the alignment frame, such that when the alignment shafts are placed and the heads and shanks are coaxial, the sensors can record the angular position of the anchors. That is, the sensors can measure, for example, the angle of the coupling relative to the alignment instrument, the position of the coupling along the length of the alignment instrument frame (e.g., to indicate the distance between adjacent alignment shafts or other components equipped with such a sensor), etc. A variety of sensors that can be used for such applications are known in the art and can include sensors, such as gyroscopes and tilt sensors used in smart phone technology.

Accordingly, the method can also include indicating and/or capturing an angular orientation of the polyaxial screw alignment instrument 1900 in a plane transverse to the longitudinal axis of the instrument, i.e., transverse to the longitudinal axis 1902. The instrument 1900 can include a transverse angle indicator, such as the bubble level 1908, to provide such an indication. The bubble level 1908 can be rotatably mounted to the elongate frame 1906 such that it rotates in a plane transverse to the longitudinal axis 1902. In the illustrated embodiment, the hemispherical bubble level 1908 can rotate in a plane perpendicular to the longitudinal axis 1902, thereby indicating the angular orientation of the instrument 1900 in the sagittal plane of the body. To use the bubble level 1908, a user can rotate the bubble level 1908 until the air bubble trapped therein indicates that the bubble level is in a level orientation. The bubble level 1908 can then be locked in this orientation, or a corresponding angular orientation can be read from a scale coupled to the bubble level 1908. One of skill in the art will appreciate that instead of a bubble level, electronic sensors, such as gyroscopes and tilt sensors used in smart phone technology can be used to capture and/or indicate angular orientation.

After capturing the position and/or angular orientation of the polyaxial screws 1602A, 1602B and attached extension tubes 1608A, 1608B, the polyaxial screw alignment instrument 1900 can be removed from the proximal ends of the tubes 1608A, 1608B. The instrument 1900 can be removed with the connection caps 1904A, 1904B and bubble level 1908 locked in their captured orientations, or the orientations can be recorded (e.g., using various distance and angular markings made on the various components of the instrument 1900) and the device removed with the connection caps and/or transverse angle indicator in an unlocked state. Moreover, in some embodiments, the extension tubes 1608A, 1608B can remain attached to the instrument 1900, and the instrument 1900 and extension tubes 1608A, 1608B can be decoupled from the receiving members 1606A, 1606B of the polyaxial screws 1602A, 1602B. Further, the alignment shafts 1702A, 1702B can also be removed and the spinal fixation procedure can proceed as known in the art.

If a surgeon or other user desires to return the polyaxial screws 1602A, 1602B to a coaxial orientation at a later point in the procedure (e.g., after shaft capture and before applying corrective forces to the screws to adjust the position and/or orientation of the vertebra), the polyaxial screw alignment instrument 1900 can be used on its own to return the screws to the desired orientation. This can be advantageous because the alignment shafts 1702A, 1702B cannot be used due to the shaft or other spinal fixation element seated within the receiving members 1606A, 1606B of the screws.

To return the polyaxial screws to a coaxial orientation, the polyaxial screw alignment instrument 1900 can be re-coupled to the proximal ends of the extension tubes 1608A, 1608B in the same manner as described above. In order to do so, a surgeon can adjust the position of each extension tube 1608A, 1608B (and thus, each receiving member 1606A, 1606B) to match up with the locked positions and orientations of the connection caps 1904A, 1904B. Alternatively, if the connection caps 1904A, 1904B were unlocked upon removal of the instrument 1900, the caps can be reattached to the extension tubes 1608A, 1608B and then repositioned until the distance and angle markings on the instrument 1900 match those recorded when the alignment shafts 1702A, 1702B were in place.

Adjusting the extension tubes 1608A, 1608B as described above will return the extension tubes to the correct orientation relative to the longitudinal axis 1902 of the instrument 1900, i.e., relative to the transverse plane of the body. In order to complete the positioning of the polyaxial screws 1602A, 1602B, the instrument 1900 (and thus the connected extension tubes 1608A, 1608B) can be adjusted in a plane transverse to the longitudinal axis 1902, i.e., in the sagittal plane of the body, until the bubble level 1908 of the transverse angle indicator matches the previously-captured orientation.

Once this is completed, a surgeon can be sure that the components of each of the polyaxial screws 1602A, 1602B are in coaxial alignment despite the absence of the alignment shafts 1702A, 1702B. In some embodiments, a surgeon can lock each of the polyaxial screws 1602A, 1602B in this orientation by inserting a set screw (e.g., the outer set screw 214 of FIG. 2) through the extension tubes 1608A, 1608B to lock the orientation of the receiving member and threaded shank.

Figure 20:
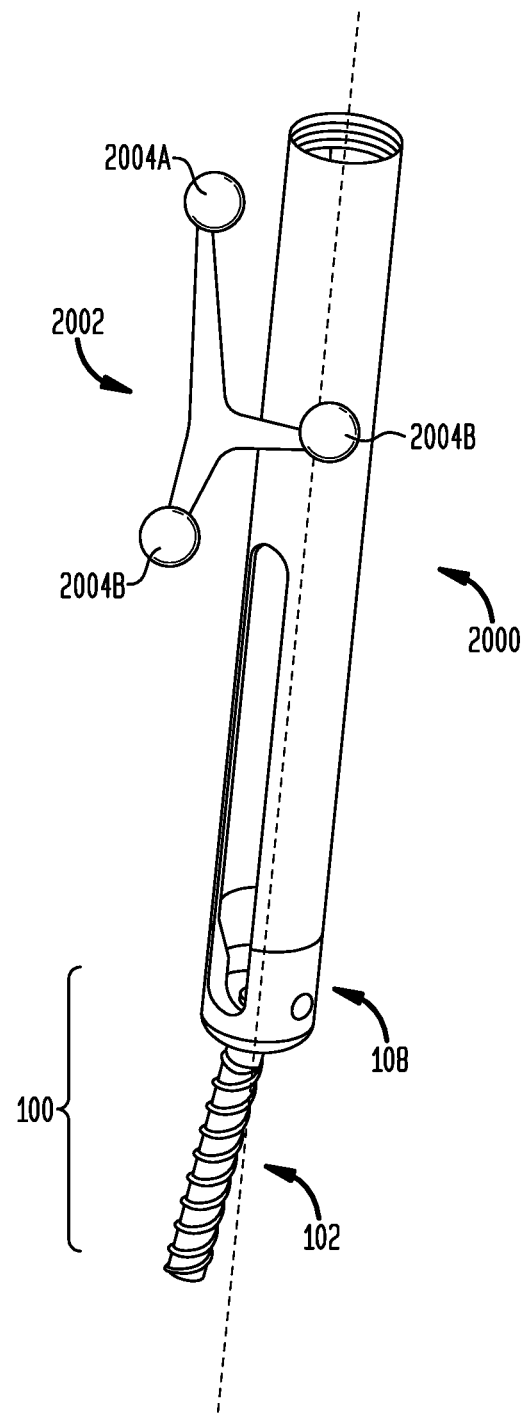
FIG. 20 is a perspective view of one embodiment of a polyaxial screw extension tube including features recognizable by an image guidance system (IGS)

In another embodiment, a method for aligning polyaxial bone screws can utilize an image guidance system (IGS) or other precision positioning system that can identify the position and orientation of surgical devices within an operating space. FIG. 20 illustrates one embodiment of a polyaxial screw extension tube 2000 that includes an array 2002 of reflective members 2004A, 2004B, 2004C positioned in a predetermined arrangement that can be recognized by an image guidance system. The screw extension tube 2000 can be similar to the screw extension tube 400 described above, save for the presence of the array 2002.

An exemplary image guidance system can also include, for example, a stereoscopic infrared (IR) camera capable of visualizing the reflective members 2004A, 2004B, 2004C of the array 2000. By visualizing the reflective members, the system can utilize their predetermined arrangement in the array 2002 to determine the exact position and orientation of the extension tube 2000 in the operating space.

As an alternative to such an image guidance system, one of skill in the art will appreciate that "smart" extension tubes, which are able to determine and record a set position and orientation, can be utilized. For example, position and/or angular sensors may be placed on the extension tubes. Once a desired orientation is established for the alignment shaft, a surgeon or other medical professional can activate a "set" button, which will capture the orientation of the tube for a given screw and the system will record the position for future use and/or reference. A person of skill in the art will further appreciate that the sensors used in such an embodiment can be "active," rather than simply passive. That is, such sensors can actively record the position and orientation of the extension tubes and wirelessly communicate this position and orientation to an interface that provides guidance information to a surgeon.

A method for aligning polyaxial screws using such a system can include coupling an extension tube, such as the extension tube 2000, to a receiving member of a polyaxial screw, such as the receiving member 108 of the polyaxial screw 100. The method can further include coupling an alignment shaft to the polyaxial screw such that the alignment shaft maintains a longitudinal axis of the receiving member and a longitudinal axis of a threaded shank of the polyaxial screw in a coaxial orientation. For example, the alignment shaft 1702 can be inserted through the extension tube 2000 to interface with both the receiving member 108 and threaded shank 102 of the polyaxial bone screw 100 such that the components are held in coaxial alignment.

Once the threaded shank 102, receiving member 108, and extension tube 2000 are in alignment, the three-dimensional position and angular orientation of the extension tube 2000 can be measured using the surgical image guidance system. That is, the reflective members 2004A, 2004B, 2004C can be imaged and the position of the extension tube 2000 can be calculated.

A surgeon can then remove the alignment shaft 1702 and proceed with the spinal procedure as known in the art. For example, the surgeon can proceed to pass a spinal fixation element through the receiving member 108 of the polyaxial screw 100. If the surgeon desires to return the components of the polyaxial screw 100 to coaxial alignment, the method can include measuring the three-dimensional position and angular orientation of the extension tube 2000 using the surgical image guidance system a second time. The surgical image guidance system can then calculate the difference between the measurements of the position and orientation of the extension tube 2000 and provide direction to the surgeon to aid in returning the polyaxial screw 100 to a coaxial orientation. The direction provided by the system can include, for example, visual and auditory prompts that include changes in direction, distance, and angle necessary to return the polyaxial screw to a coaxial orientation. In response, the surgeon can adjust the extension tube 2000 to place the longitudinal axis of the receiving member 108 and the longitudinal axis of the threaded shank 102 in a coaxial orientation based on guidance from the surgical image guidance system. This process can be repeated as many times as necessary to move the extension tube 2000 (and coupled polyaxial screw 100) into a coaxial orientation.

Following repositioning, the method can include, in some embodiments, inserting a set screw into the receiving member 108 of the polyaxial screw 100 after adjusting the extension tube 2000 to achieve a coaxial orientation of the receiving member 108 and the threaded shank 102. The set screw, such as the outer set screw 214 shown in FIG. 2, can independently lock the orientation of the receiving member 108 relative to the threaded shank 102 while still allowing the receiving member 108 to move relative to a captured spinal fixation element in response to corrective forces applied by a surgeon.

The methods and devices described herein can be utilized in a variety of operations—both in the spine and in other areas of the body. In the embodiments described above, reference is made to two polyaxial screws bilaterally implanted in a single vertebral body. While this is one example of a configuration of one or more polyaxial bone screws, additional configurations are also possible. Furthermore, in the embodiments described above, reference is made to the polyaxial screw alignment instrument being applied such that a longitudinal axis of the instrument lies within the transverse plane of the body and such that the transverse angle indicator measures an angular orientation in the sagittal plane of the body. This is also one of several possible orientations for use of the devices and methods described herein.

Figure 21:
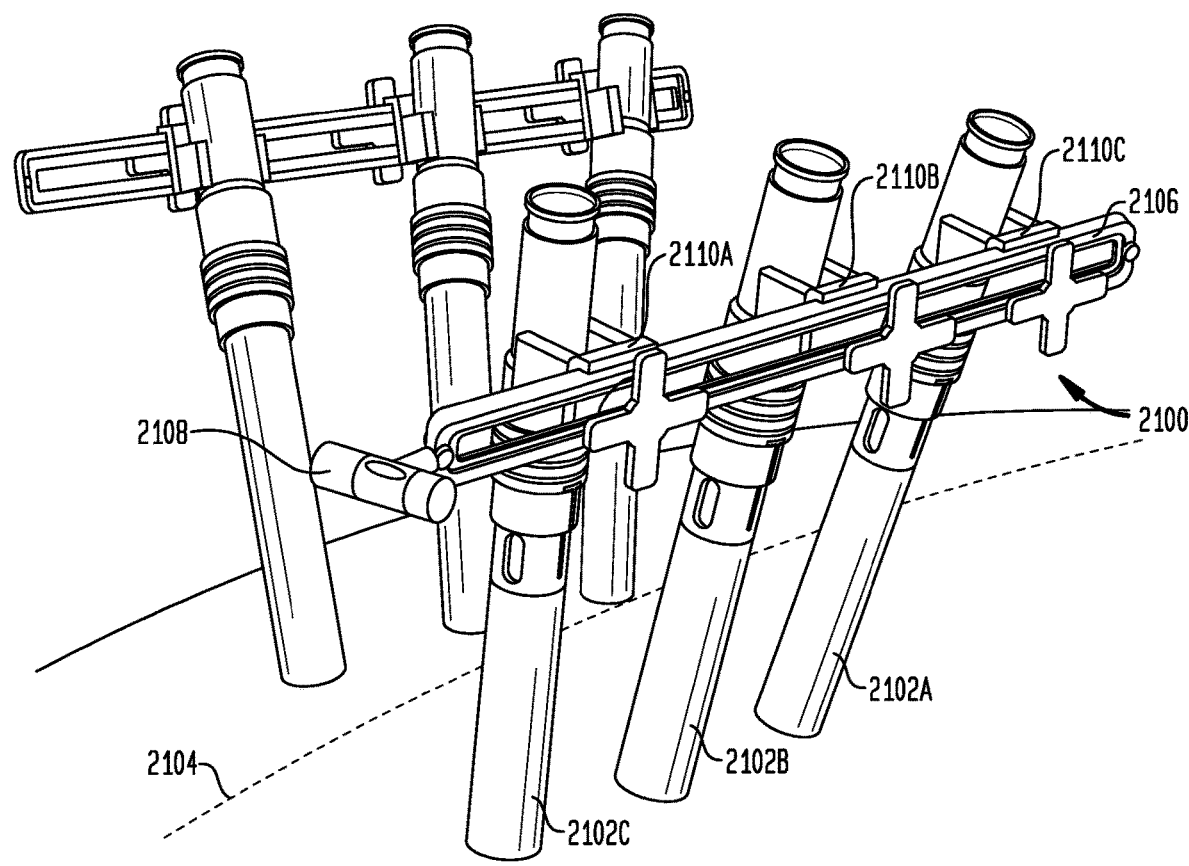
FIG. 21 is an alternative embodiment of a polyaxial screw alignment instrument.

FIG. 21, for example, illustrates an alternative embodiment of a polyaxial screw alignment instrument 2100 that is coupled to a plurality of polyaxial screw extension tubes 2102A, 2102B, 2102C that are implanted in a plurality of adjacent vertebrae on one side of the spinal column 2104. In this embodiment, the longitudinal axis of the elongate frame 2106 lies in the sagittal plane of the body and thus captures relative distances and angles between the plurality of extension tubes 2102A, 2102B, 2102C in this plane. Correspondingly, the transverse angle indicator 2108 indicates the angular orientation of the elongate frame 2106 in the transverse plane of the body. Still further, the polyaxial screw alignment instrument 2100 includes an alternative embodiment of a connection cap 2110A, 2110B, 2110C that couples to each of the screw extension tubes 2102A, 2102B, 2102C along a mid-portion thereof, rather than at a proximal end thereof. One of skill in the art will appreciate that embodiment described in FIG. 21 may not be effective when more than two polyaxial screw extension tubes are implanted on adjacent vertebral bodies. Further, one of skill in the art will appreciate that other modifications are also possible and these too are considered within the scope of the invention.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A method of aligning polyaxial screws, comprising:
   coupling an extension tube to a receiving member of a polyaxial screw, the extension tube comprising features recognizable to a surgical image guidance system;
   coupling an alignment shaft to the polyaxial screw such that the alignment shaft maintains a longitudinal axis of the receiving member and a longitudinal axis of a threaded shank of the polyaxial screw in a coaxial orientation;
   imaging the features of the extension tube using a camera of the surgical guidance system; and
   measuring, based on the imaging and a predetermined arrangement of the features, the three-dimensional position and angular orientation of the extension tube using the surgical image guidance system.

2. The method of claim 1, further comprising:
   removing the alignment shaft from the polyaxial screw after measuring the three-dimensional position and angular orientation of the extension tube;

passing a spinal fixation element through the receiving member of the polyaxial screw;

measuring the three-dimensional position and angular orientation of the extension tube using the surgical guidance system a second time; and adjusting the extension tube to place the longitudinal axis of the receiving member and the longitudinal axis of the threaded shank in a coaxial orientation based on guidance from the surgical guidance system.

3. The method of claim 2, further comprising inserting a set screw into the polyaxial screw after adjusting the extension tube to maintain the coaxial orientation of the receiving member and the threaded shank.

4. The method of claim 1, wherein the polyaxial screw is implanted in a patient's vertebra.

5. The method of claim 1, wherein the features recognizable to the surgical image guidance system comprises an array of reflective members.

6. The method of claim 5, wherein measuring the three-dimensional position and angular orientation of the extension tube using the surgical image guidance system includes the surgical image guidance system utilizing a predetermined arrangement of the array to determine an exact position and orientation of the extension tube in an operating space.

7. The method of claim 5, wherein the camera comprises a stereoscopic infrared camera.

8. The method of claim 1, wherein the features recognizable to a surgical guidance system comprise sensors configured to wireless communicate with the surgical guidance system, and wherein the measuring is further based on wireless signals received from the sensors.

9. The method of claim 8, wherein the sensors include one or more of position sensor and angular sensors.

10. The method of claim 8, wherein the sensors are configured to actively record the position and orientation of the extension tube.

11. The method of claim 10, further comprising communicating the position and orientation of the extension tube to an interface via the surgical guidance system.

12. The method of claim 8, wherein the sensors are passive sensors.

* * * * *